(12) United States Patent
Tatsutani et al.

(10) Patent No.: US 10,197,550 B2
(45) Date of Patent: Feb. 5, 2019

(54) SAMPLE PROCESSING SYSTEM

(75) Inventors: Hiroo Tatsutani, Kobe (JP); Tomoyuki Asahara, Kobe (JP)

(73) Assignee: SYSMEX CORPORATION, Kobe (JP)

( * ) Notice: Subject to any disclaimer, the term of this patent is extended or adjusted under 35 U.S.C. 154(b) by 0 days.

(21) Appl. No.: 13/015,225

(22) Filed: Jan. 27, 2011

(65) Prior Publication Data
US 2011/0189053 A1    Aug. 4, 2011

(30) Foreign Application Priority Data

Jan. 29, 2010    (JP) ................................. 2010-018819

(51) Int. Cl.
*G01N 33/48*    (2006.01)
*G01N 35/02*    (2006.01)

(52) U.S. Cl.
CPC .................................... *G01N 33/48* (2013.01)

(58) Field of Classification Search
None
See application file for complete search history.

(56) References Cited

U.S. PATENT DOCUMENTS

| | | | | |
|---|---|---|---|---|
| 6,117,683 A | * | 9/2000 | Kodama et al. | 436/47 |
| 6,290,907 B1 | * | 9/2001 | Takahashi et al. | 422/65 |
| 2001/0043882 A1 | | 11/2001 | Berger et al. | |
| 2003/0114994 A1 | * | 6/2003 | Wada | F24F 11/0086 702/33 |
| 2003/0202905 A1 | * | 10/2003 | Devlin, Sr. | G01N 35/04 422/64 |
| 2005/0036912 A1 | * | 2/2005 | Yamakawa et al. | 422/65 |
| 2005/0036913 A1 | * | 2/2005 | Yamakawa et al. | 422/65 |
| 2005/0196320 A1 | * | 8/2005 | Veiner et al. | |

FOREIGN PATENT DOCUMENTS

| | | |
|---|---|---|
| JP | 07-306065 A | 11/1995 |
| JP | 09-243646 A | 9/1997 |
| JP | 11-264828 A | 9/1999 |
| JP | 11-316236 A | 11/1999 |
| JP | 2001-242179 A | 9/2001 |
| JP | 2005-241612 A | 9/2005 |

* cited by examiner

*Primary Examiner* — Kathryn Wright
(74) *Attorney, Agent, or Firm* — Brinks Gilson & Lione

(57) ABSTRACT

A sample processing system comprising: a plurality of sample processing units; and a transport apparatus for transporting a sample to any of the plurality of sample processing units, wherein the transport apparatus comprises a communication section for communicating with an apparatus external to the transport apparatus and a controlling section for setting the transport apparatus in a start-up state when the communication section have received a start-up command signal from the external apparatus.

10 Claims, 15 Drawing Sheets

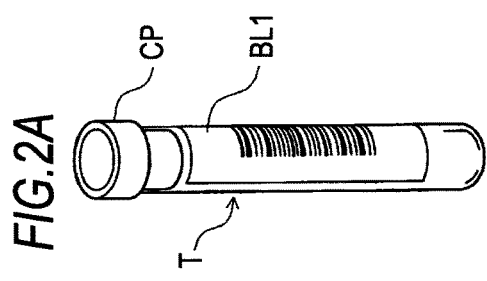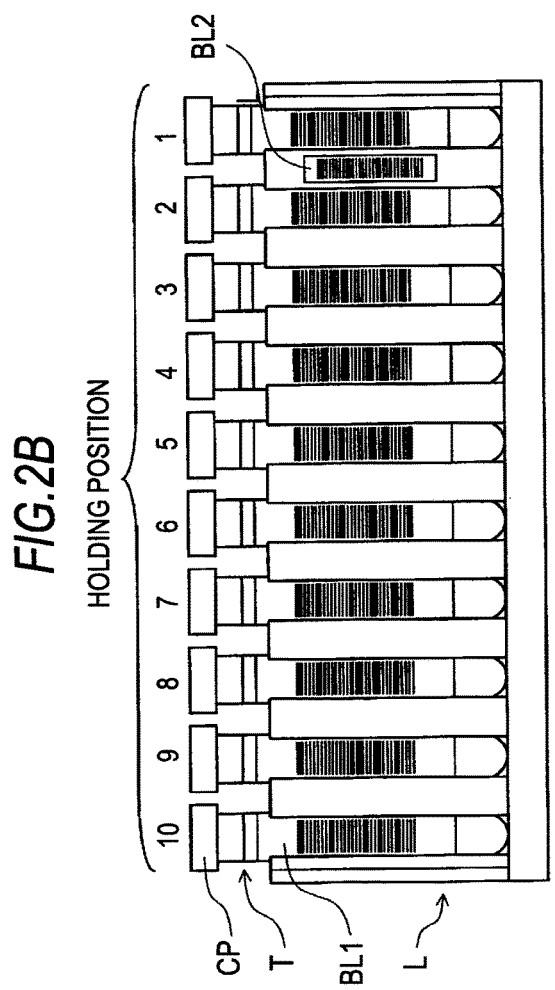

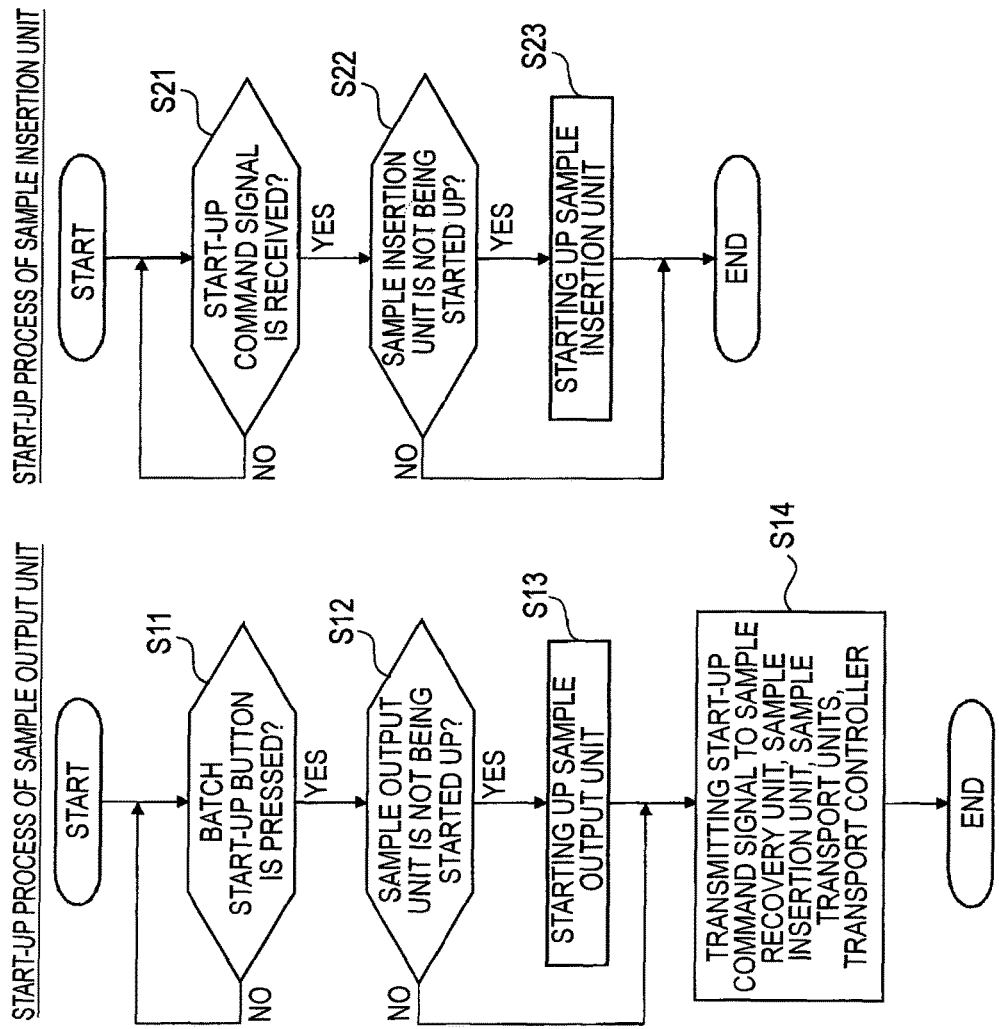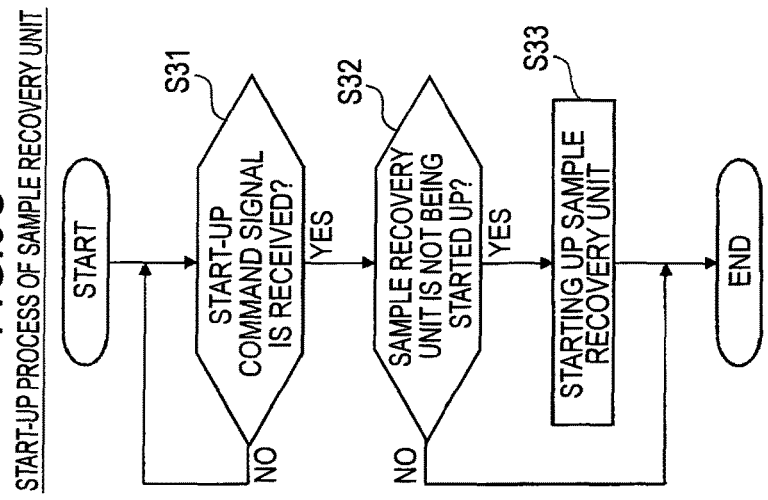

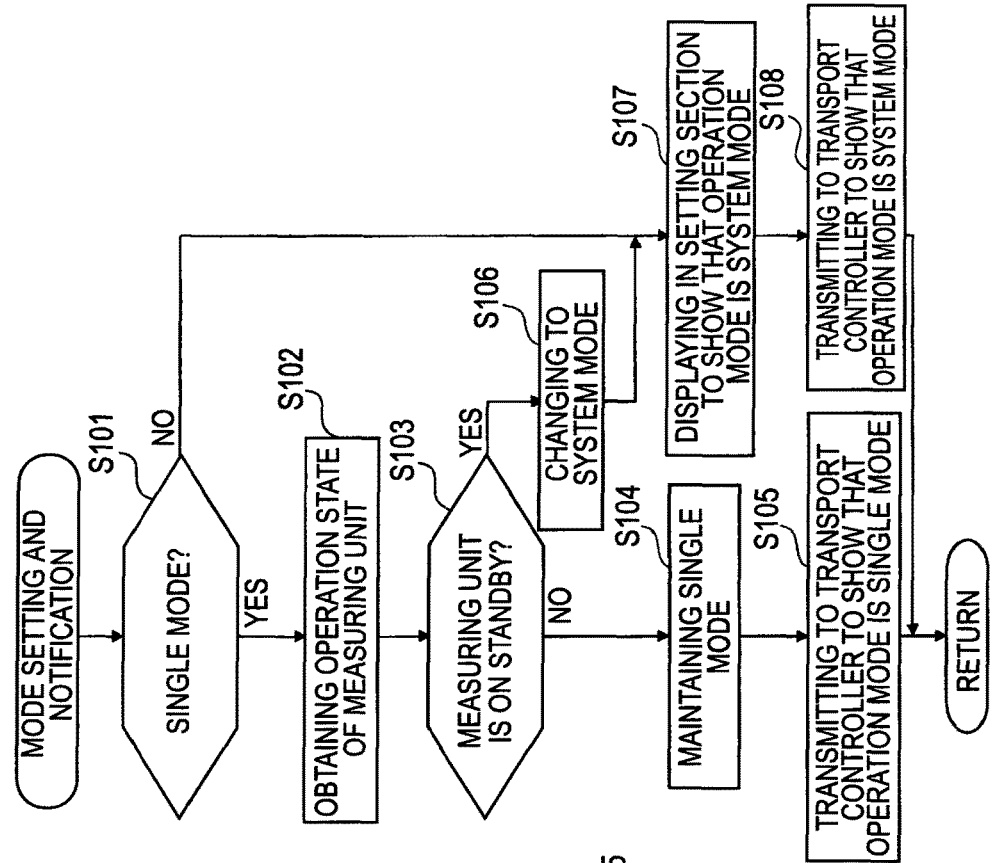
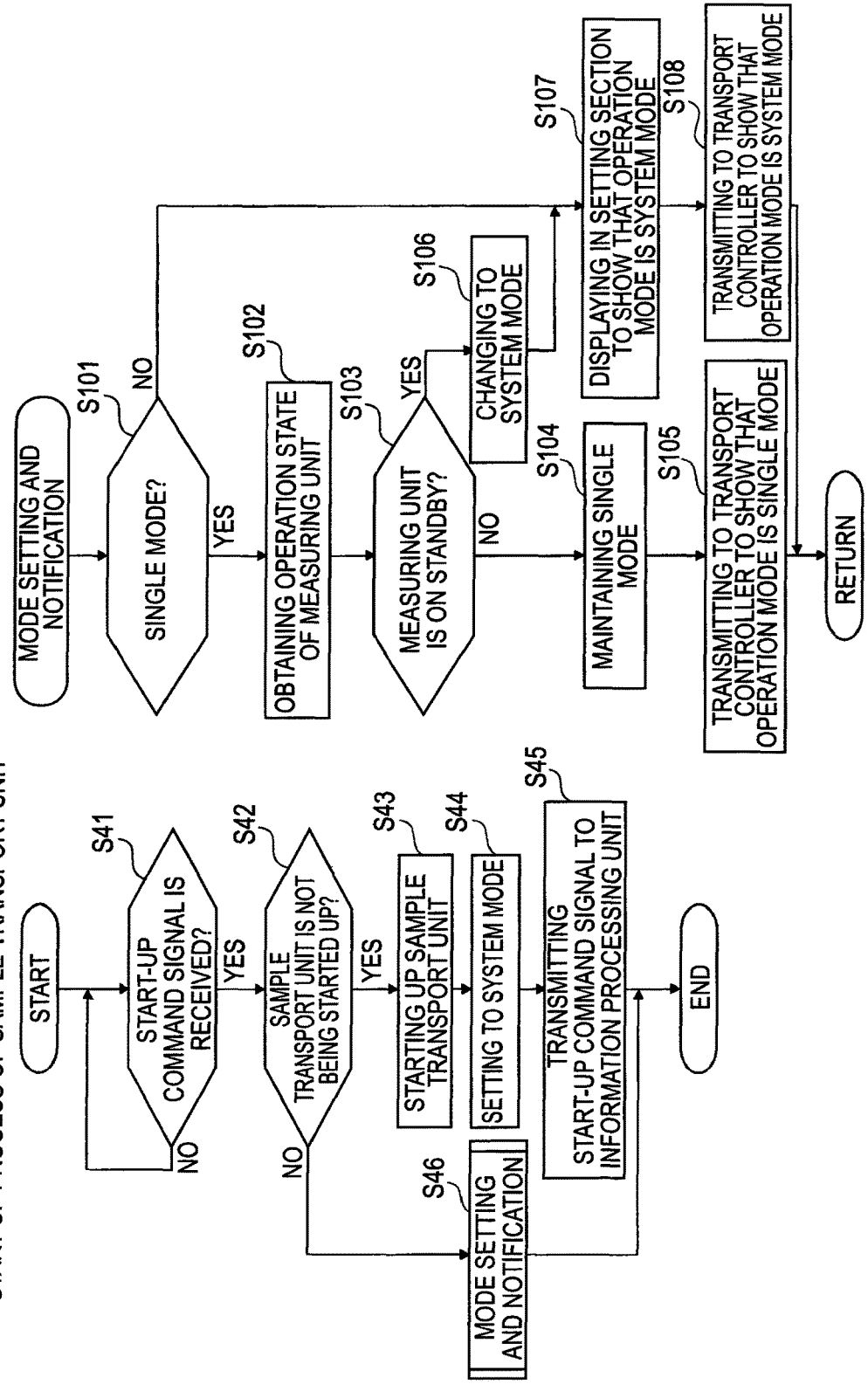

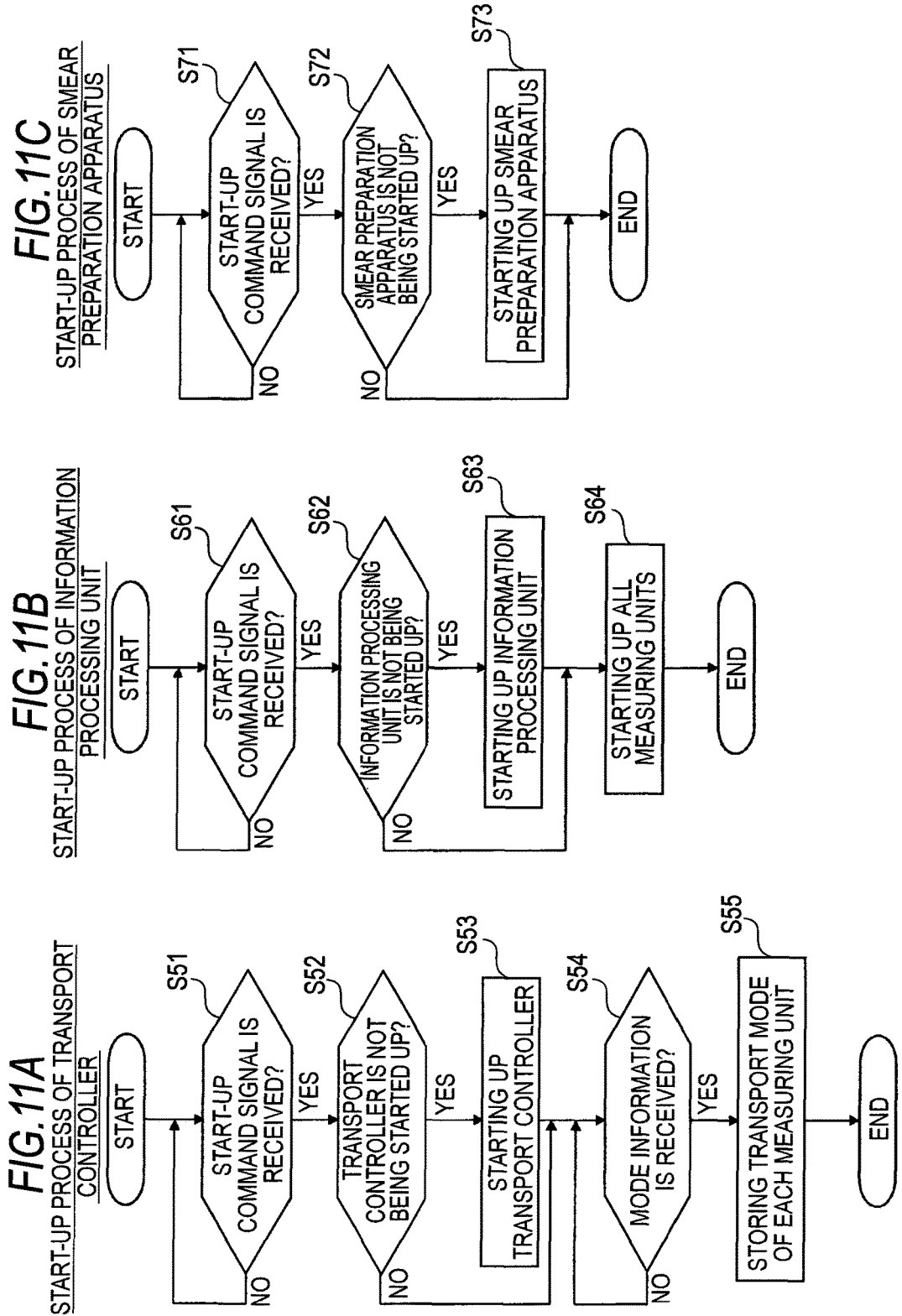

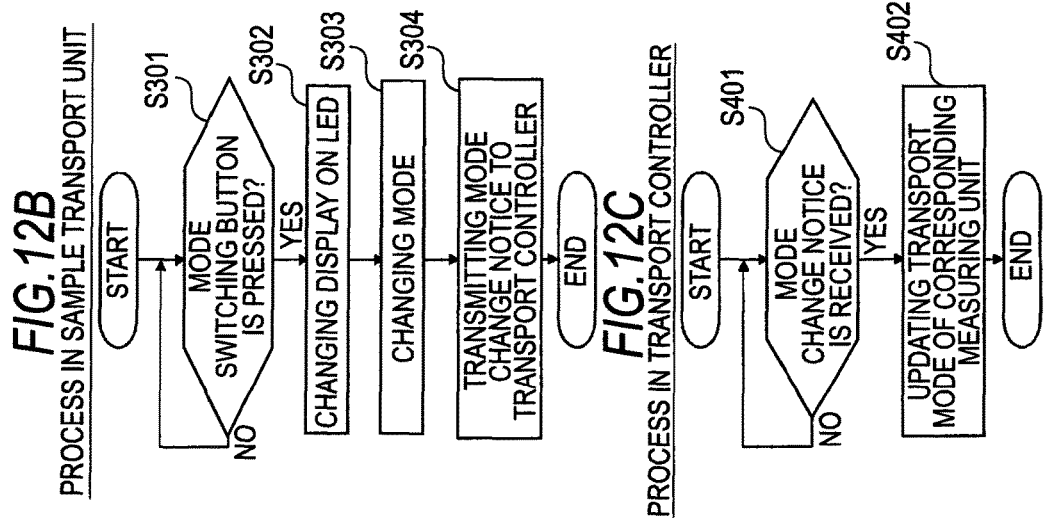
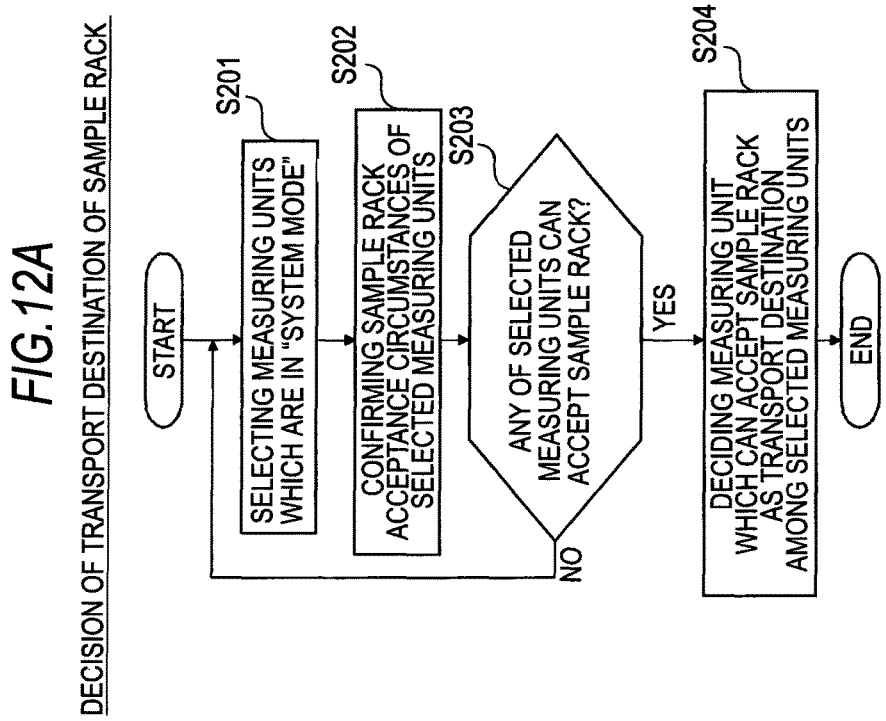

START-UP PROCESS OF TRANSPORT CONTROLLER

START-UP PROCESS OF SAMPLE OUTPUT UNIT

START-UP PROCESS OF INFORMATION PROCESSING UNIT

START-UP PROCESS OF SAMPLE OUTPUT UNIT

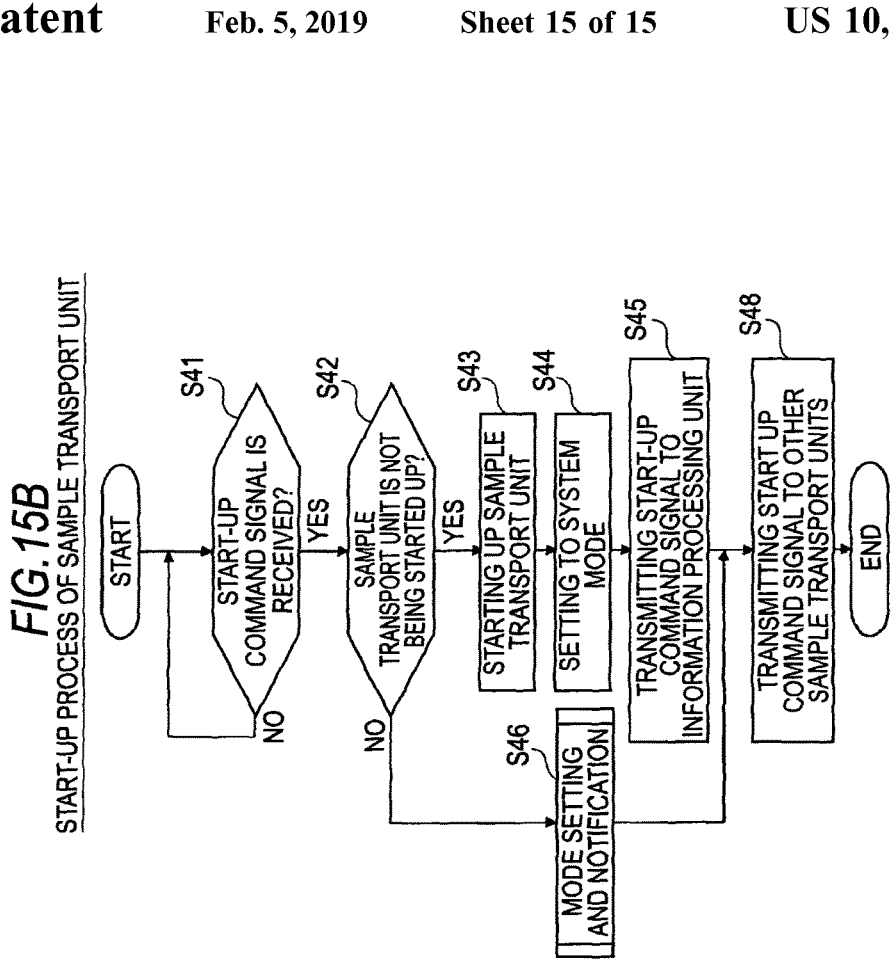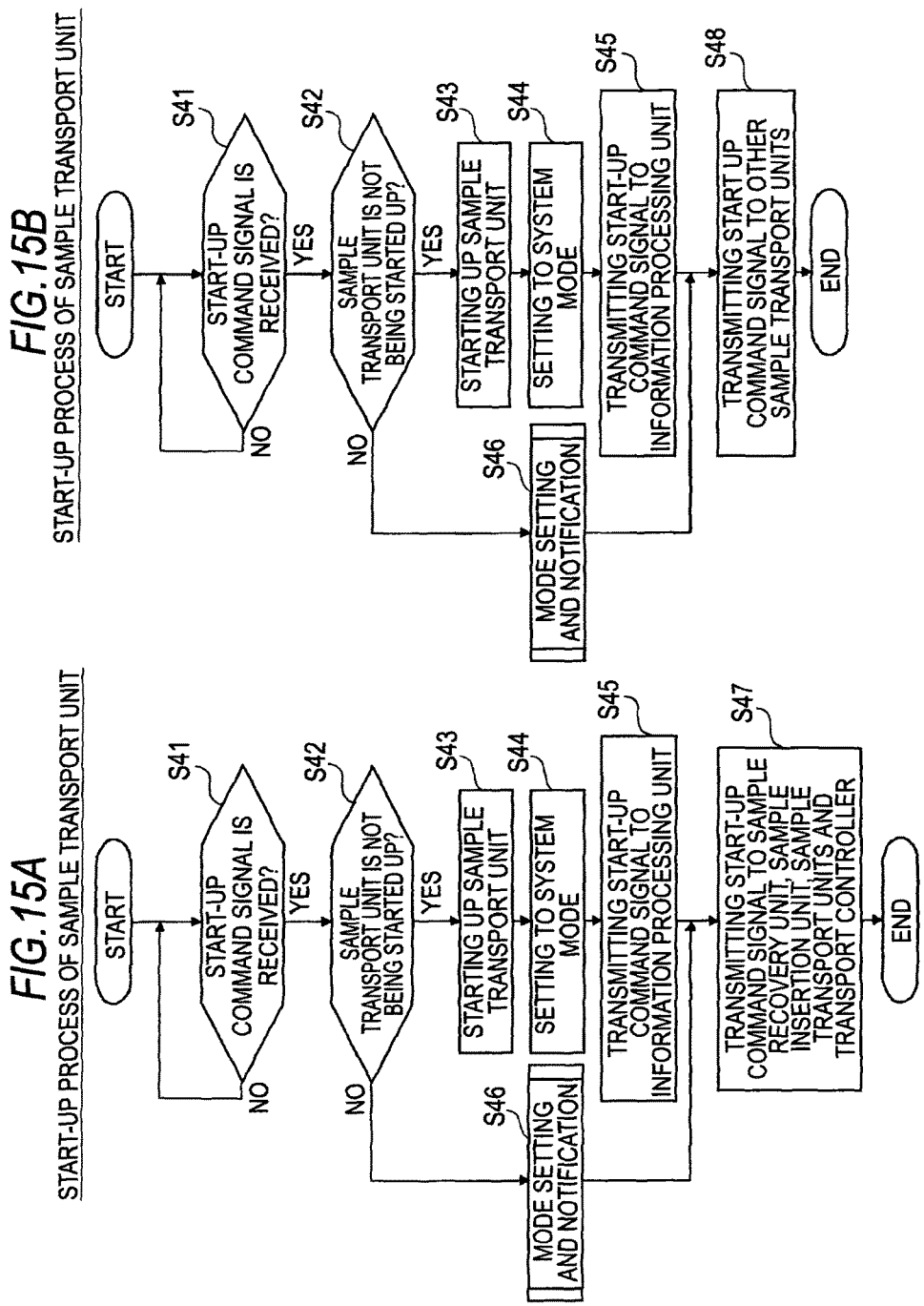

SAMPLE PROCESSING SYSTEM

RELATED APPLICATIONS

This application claims priority under 35 U.S.C. § 119 to Japanese Patent Application No. 2010-018819 filed on Jan. 29, 2010, the entire content of which is hereby incorporated by reference.

FIELD OF THE INVENTION

The present invention relates to a sample processing system including a plurality of sample processing apparatuses and a transport apparatus for transporting samples to the plurality of sample processing apparatuses.

BACKGROUND OF THE INVENTION

Conventionally, a sample processing system has been known which includes a plurality of sample analysis apparatuses for analyzing a sample such as blood, urine and so on and a transport apparatus for transporting samples to the plurality of sample analysis apparatuses. In such a sample processing system, it is necessary to separately manipulate the start-up of each apparatus.

Japanese Laid-Open Patent Publication No. H11-316236 discloses a sample analysis system in which a plurality of analysis apparatuses and a transport apparatus are connected to a total control computer. In Japanese Laid-Open Patent Publication No. H11-316236, it is also described that the start-up of each analysis apparatus can be instructed by the key manipulation of a manipulation section.

However, in Japanese Laid-Open Patent Publication No. H11-316236, there is no description of the start-up of the transport apparatus. In addition, in Japanese Laid-Open Patent Publication No. H11-316236, there is no description of a specific configuration for starting up each analysis apparatus by the key manipulation of the manipulation section, and the start-up manipulation by a user was not able to be simplified.

SUMMARY OF THE INVENTION

The scope of the present invention is defined solely by the appended claims, and is not affected to any degree by the statements within this summary.

According to a first aspect of the present invention, a sample processing system comprising: a plurality of sample processing units; and a transport apparatus for transporting a sample to any of the plurality of sample processing units, wherein the transport apparatus comprises a communication section for communicating with an apparatus external to the transport apparatus and a controlling section for setting the transport apparatus in a start-up state when the communication section have received a start-up command signal from the external apparatus.

According to a second aspect of the present invention, a sample processing system comprising: a plurality of sample processing units; a sample processing control unit for controlling at least one of the plurality of sample processing units; and a transport apparatus for transporting a sample to any of the plurality of sample processing units, wherein the sample processing control unit comprises a communication section for communicating with an apparatus external to the sample processing control unit and a controlling section for setting the sample processing control unit in a start-up state when the communication section has received a start-up command signal from the external apparatus.

According to a third aspect of the present invention, a sample processing system comprising: a plurality of sample processing units; a transport apparatus for transporting a sample to any of the plurality of sample processing units; and a transport control unit for controlling the transport apparatus, wherein the transport control unit comprises a communication section for communicating with an apparatus external to the transport control unit and a controlling section for setting the transport control unit in a start-up state when the communication section has received a start-up command signal from the external apparatus.

BRIEF DESCRIPTION OF THE DRAWINGS

FIG. 2A is a perspective view showing the appearance of a sample container according to the embodiment.

FIG. 2B is a front view of a sample rack according to the embodiment.

FIG. 9A is a flowchart showing the start-up process of the sample output unit according to the embodiment.

FIG. 9B is a flowchart showing the start-up process of the sample insertion unit according to the embodiment.

FIG. 9C is a flowchart showing the start-up process of a sample recovery unit according to the embodiment.

FIGS. 10A and 10B are flowcharts showing the start-up process of the sample transport unit according to the embodiment.

FIG. 11A is a flowchart showing the start-up process of the transport controller according to the embodiment.

FIG. 11B is a flowchart showing the start-up process of the information processing unit according to the embodiment.

FIG. 11C is a flowchart showing the start-up process of the smear preparation apparatus according to the embodiment.

FIG. 12A is a flowchart showing a process for deciding the transport destination of a sample rack according to the embodiment.

FIG. 12B and FIG. 12C are flowcharts showing a process in mode switching according to the embodiment.

FIGS. 15A and 15B are modified examples of the flowchart showing the start-up process of the sample transport unit according to the embodiment.

DETAILED DESCRIPTION OF THE PREFERRED EMBODIMENTS

This embodiment is a sample processing system for examination and analysis related to blood, to which the present invention is applied. A sample processing system according to this embodiment includes three measuring units and one smear preparation apparatus. In the three measuring units, blood analysis is performed in parallel, and when it is necessary to prepare a smear based on the analysis result thereof, the smear preparation apparatus prepares a smear.

Hereinafter, a sample processing system according to this embodiment will be described with reference to the drawings.

Figure 1:
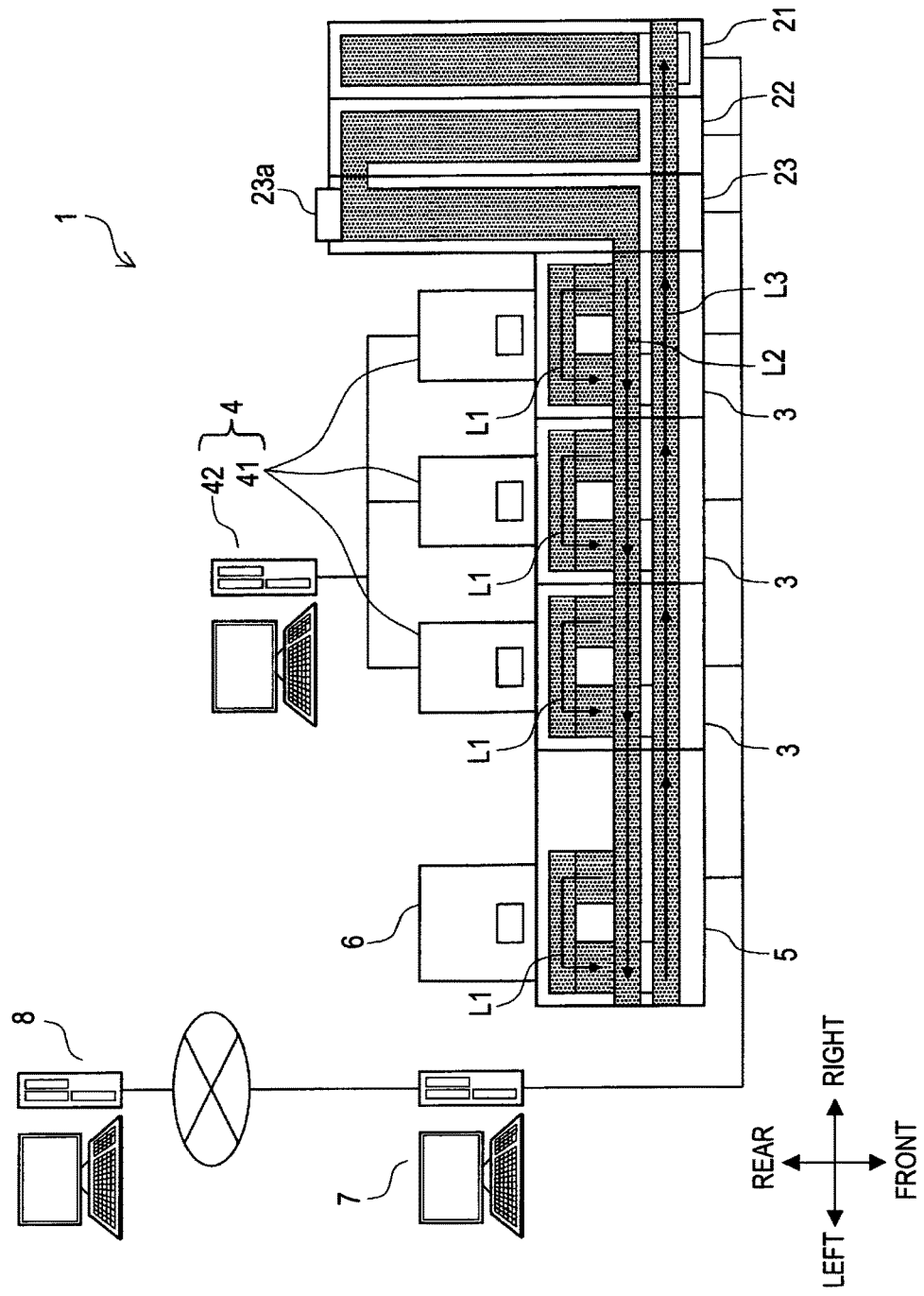
FIG. 1 is a diagram showing the configuration of a sample processing system according to an embodiment.

FIG. 1 is a plan view showing the configuration when a sample processing system 1 is viewed from the upper side. The sample processing system 1 according to this embodiment is configured to include a sample recovery unit 21, a sample insertion unit 22, a sample output unit 23, three sample transport units 3, a blood cell analysis apparatus 4, a sample transport unit 5, a smear preparation apparatus 6 and a transport controller 7. In addition, the sample processing system 1 of this embodiment is connected to a host computer 8 via a communication network so as to communicate therewith.

Each of the sample recovery unit 21, the sample insertion unit 22 and the sample output unit 23 is configured so that a plurality of sample racks can be placed therein.

FIG. 2 is a diagram showing the configurations of a sample container T and a sample rack L. FIG. 2A is a perspective view showing the appearance of a sample container T and FIG. 2B is a front view of a sample rack L.

A sample container T is a tubular container made of glass or a synthetic resin having translucency and the upper end thereof is opened. In the sample container, a blood sample collected from a patient is contained and the opening of the upper end is sealed by a cap section CP. A bar-code label BL1 is adhered to a side surface of the sample container T. A bar-code showing a sample ID is printed on the bar-code label BL1.

In a sample rack L, ten holding positions are formed so as to arrange and hold ten sample containers T in a vertical state (erect state). In addition, as shown in FIG. 2B, a bar-code label BL2 is adhered to a front surface of the sample rack L. A bar-code showing a rack ID is printed on the bar-code label BL2.

Returning to FIG. 1, the sample recovery unit 21 stores sample racks L in which analysis has ended. The sample insertion unit 22 stores sample racks L which are inserted by an operator, and outputs the stored sample racks L to the sample output unit 23. In addition, the sample recovery unit 21 and the sample insertion unit 22 are connected to the sample output unit 23 and the transport controller 7 so as to communicate therewith.

The sample output unit 23 includes a bar-code reading section 23a. By the bar-code reading section 23a, a rack ID of a sample rack L which is output from the sample insertion unit 22 and a sample ID of a sample container T which is associated with a holding position in the sample rack L are read. The sample output unit 23 outputs a sample rack L in which the reading of the bar-code has been completed to the sample transport unit 3. In addition, the sample output unit 23 is connected to the sample recovery unit 21, the sample insertion unit 22, the three sample transport units 3, the sample transport unit 5 and the transport controller 7 so as to communicate therewith, and the rack ID and the sample ID which are read by the sample output unit 23 are transmitted to the transport controller 7.

In addition, the sample output unit 23 includes a batch start-up button to be described later. When an operator pushes the batch start-up button, the units (apparatuses) in the sample processing system 1 are started up. Such a batch start-up button will be described later with reference to FIG. 5.

The three sample transport units 3 are disposed in front of three measuring units 41, respectively, as shown in FIG. 1. The neighboring two sample transport units 3 are connected to each other so as to deliver sample racks L. The right end of the sample transport unit 3 on the right side is connected to the sample output unit 23 so as to deliver sample racks L, and the left end of the sample transport unit 3 on the left side is connected to the sample transport unit 5 so as to deliver sample racks L. In addition, the three sample transport units 3 are respectively connected to the sample output unit 23, an information processing unit 42 and the transport controller 7 so as to communicate therewith.

As shown in FIG. 1, in these three sample transport units 3, two transport lines L1 and L2 for transporting sample racks L are set by dividing cases into the case in which the measurement of a sample is performed in the respective corresponding measuring units 41 and the case in which the measurement is not performed. That is, when the measurement of a sample is performed by the measuring unit 41, a sample rack L is transported along the transport line L1 shown by the rear arrow. When the measurement of a sample is not performed in the measuring unit 41 but is performed in the measuring unit 41 on the downstream side (left side), a sample rack L is transported along the transport line L2 shown by the intermediate left-pointing arrow so as to skip the present measuring unit 41.

When the measurement of a sample is performed in the corresponding measuring unit 41, each sample transport unit 3 receives a measurement order from the transport controller 7. Such a measurement order is transmitted to the information processing unit 42.

In addition, in each sample transport unit 3, a transport line L3 for transporting sample racks L to the sample recovery unit 21 is set as shown in FIG. 1. That is, a sample rack L, in which measurement has ended or preparation of a smear has ended, is transported along the transport line L3 shown by the front right-pointing arrow and is recovered by the sample recovery unit 21. The configuration of the sample transport unit 3 will be described later with reference to FIG. 3.

The blood cell analysis apparatus 4 is an optical flow cytometry type multiple blood cell analysis apparatus and includes the three measuring units 41 and the information processing apparatus 42. The information processing unit 42 is connected to the three measuring units 41 so as to communicate therewith, and controls the operations of the three measuring units 41. In addition, the information processing unit 42 is also connected to the three sample transport units 3 so as to communicate therewith.

The three measuring units 41 measure a blood sample which is contained in a sample container T on the basis of the measurement order received by the information processing unit 42. In such measurement, each measuring unit 41 takes a sample container T from a sample rack L at a predetermined position on the transport line L1 of the sample transport unit 3 disposed in front of the measuring unit. The blood sample contained in the sample container T is measured in the measuring unit 41. When the measurement in the measuring unit 41 is completed, the sample container T returns to the original holding position in the sample rack L.

The sample transport unit 5 is disposed in front of the smear preparation apparatus 6. As in the sample transport unit 3, transport lines L1, L2 and L3 are set in the sample transport unit 5. In addition, the sample transport unit 5 is connected to the sample output unit 23, the smear preparation apparatus 6 and the transport controller 7 so as to communicate therewith.

In the smear preparation apparatus 6, a smear of a blood sample is prepared. That is, first, the smear preparation apparatus 6 suctions a blood sample contained in a sample container T at a predetermined position on the transport line L1 of the sample transport unit 5. Next, the suctioned blood sample is dropped onto a glass slide, thinly extended on the glass slide and then is dried. After that, a liquid dye is supplied to the glass slide to dye the blood on the glass slide and a smear is prepared. In addition, the smear preparation apparatus 6 is connected to the sample transport unit 5 so as to communicate therewith and the driving thereof is controlled in response to the instruction of the sample transport unit 5.

Whether the preparation of a smear is required is determined by the transport controller 7 on the basis of the result of the analysis which is performed by the information processing unit 42, based on the result of the measurement in the three measuring units 41. The result of the analysis which is performed by the information processing unit 42 is transmitted to the transport controller 7 via the sample transport unit 3. When the transport controller 7 determines that the preparation of a smear is required, the sample rack L storing a target sample is transported along the transport line L1 of the sample transport unit 5 and a smear is prepared in the smear preparation apparatus 6.

The transport controller 7 is connected to the sample recovery unit 21, the sample insertion unit 22, the sample output unit 23, the three sample transport units 3 and the sample transport unit 5 so as to communicate therewith and controls the driving of each unit. As the transport controller 7, for example, a separate personal computer or a computer incorporated in the system is used.

When receiving the rack ID of a sample rack L, the sample ID of a sample container T and the holding position of the sample container T from the sample output unit 23, the transport controller 7 inquires of the host computer 8 for a measurement order. When receiving the measurement order from the host computer 8, the transport controller 7 stores the measurement order in association with the rack ID, the sample ID and the holding position.

In addition, the transport controller 7 determines whether the sample rack L which is output from the sample output unit 23 is transported to any of the three measuring units 41. The transport controller 7 controls each sample transport unit 3 so as to transport the sample rack L to the measuring unit 41 decided as the transport destination. The transport controller 7 transmits the stored measurement order to the sample transport unit 3 corresponding to the measuring unit 41 decided as a transport destination.

The host computer 8 is connected to the communication network and can communicate with the transport controller 7. In a storage section of the host computer 8, measurement orders are stored. When the transport controller 7 requests a measurement order including a sample ID, the host computer 8 reads out the measurement order corresponding to this sample ID from the storage section and transmits the measurement order to the transport controller 7.

Here, in the three measuring units 41, the operation mode is set to either a "single mode" or a "system mode". When the operation mode of the measuring units 41 is set to the "system mode", as described above, the sample rack L which is output from the sample output unit 23 is transported to any one of the measuring units 41 in which the "system mode" is set. When the operation mode of the measuring units 41 is set to the "single mode", this measuring unit 41 is not included in the destination of the sample rack L which is output from the sample output unit 23. That is, when the operation mode of the measuring unit 41 is set to the "single mode", the sample rack L which is output from the sample output unit 23 is transported along the transport line L2 and is not positioned in front of this measuring unit 41.

When the operation mode of the measuring unit 41 is set to the "single mode", the sample rack L on the transport line L1 of this measuring unit 41 is transported singly on the transport line L1, separately from the sample rack L which is output from the sample output unit 23. Accordingly, an operator can independently measure the sample rack L on the transport line L1.

Also in the sample transport unit 5, the operation mode is set to either a "single mode" or a "system mode". When the operation mode of the sample transport unit 5 is set to the "system mode" and it is determined that the preparation of a smear is required on the basis of the measurement result of the measuring unit 41 as described above, the sample rack L is positioned in front of the smear preparation apparatus 6 along the transport line L1 of the sample transport unit 5. When the operation mode of the sample transport unit 5 is set to the "single mode", regardless of whether the preparation of a smear is required, the sample rack L which is measured by the measuring unit 41 is transported toward the sample recovery unit 21 before being introduced to the sample transport unit 5 and is not positioned in front of the smear preparation apparatus 6. Accordingly, an operator can independently prepare a smear with respect to the sample rack L on the transport line L1.

Figure 3:
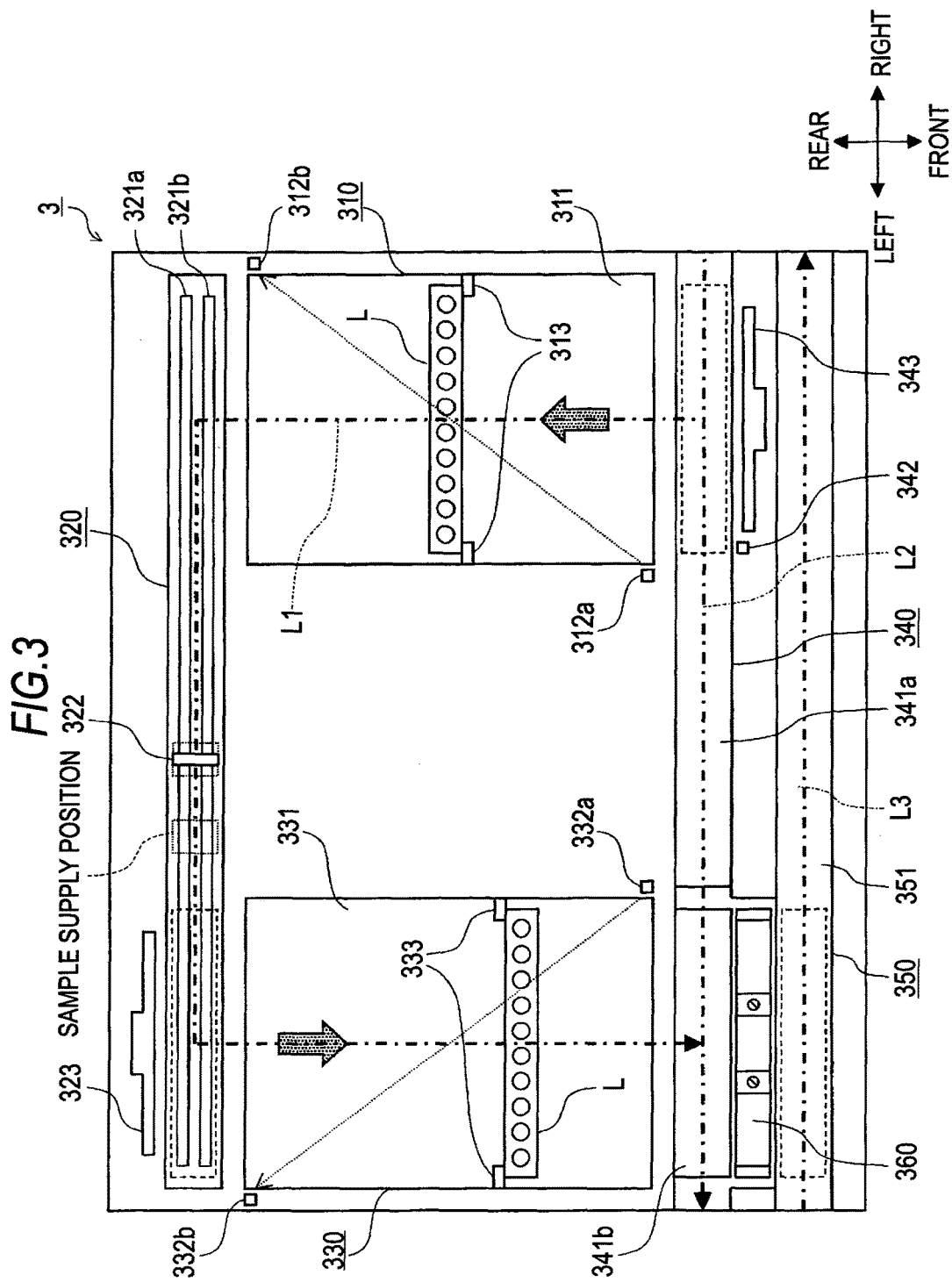
FIG. 3 is a plan view showing the configuration of a sample transport unit according to the embodiment.

FIG. 3 is a plan view showing the configuration when the sample transport unit 3 is viewed from the upper side. The sample transport unit 3 includes a pre-analysis rack holding section 310, a rack transport section 320, a post-analysis rack holding section 330 and rack transport sections 340 and 350.

When the operation mode of the measuring unit 41 corresponding to this sample transport unit 3 is the "system mode" and the measurement of a sample rack L output from the upstream side (right side) is not performed in the corresponding measuring unit 41, this sample rack L is linearly sent to the left end from the right end of the rack transport section 340 along the transport line L2 by belts 341*a* and 341*b* of the rack transport section 340.

When the operation mode of the measuring unit 41 corresponding to this sample transport unit 3 is the "system mode" and the measurement related to a sample rack L output from the upstream side (right side) is performed in the corresponding measuring unit 41, this sample rack L is sent to the right end position of the rack transport section 340 shown by the broken line in the right lower portion of FIG. 3. That is, when a reflective sensor 342 shown in FIG. 3 detects that the sample rack L has been transported to the position shown by the broken line in the right lower portion of FIG. 3, the belt 341*a* is stopped at this timing. After that, by moving a rack pushing mechanism 343 backward, the sample rack L is pushed to the front end of a transport passage 311 of the pre-analysis rack holding section 310.

When optical sensors 312*a* and 312*b* including a light-emitting section and a light-receiving section detect the sample rack L on the transport passage 311, a rack sending mechanism 313 moves backward while coming into contact with the front ends of the sample rack L and the sample rack L is sent to the back. In this manner, when the sample rack L is sent up to the right end position of the rack transport section 320, belts 321*a* and 321*b* are driven and the sample rack L is sent in the left direction.

After that, the sample rack L arrives at the position of a sample container sensor 322. The sample container sensor 322 is a contact sensor. When a detection target sample container T, which is held in the sample rack L, passes through the position under the sample container sensor 322, the contact piece of the sample container sensor 322 is bent by the sample container T and thus the presence of the sample container T is detected.

At a sample supply position positioned on the left side of the position, at which the sample container T has been detected by the sample container sensor 322, by a distance corresponding to two sample containers, a hand section of the measuring unit 41 which will be described later grips the sample container T and takes the sample container T from the sample rack L. The removed sample container T returns to the sample rack L after being used in the measurement in the measuring unit 41. While the sample container T returns to the sample rack L, the transportation of the sample rack L is on standby.

In this manner, when the measurement of the samples in all of the sample containers T held in the sample rack L is completed, the sample rack L is sent up to the left end position of the rack transport section 320 shown by the broken line in FIG. 3 by the belts 321*a* and 321*b* and the driving of the belts 321*a* and 321*b* is stopped.

Then, the sample rack L is sent to the rear end of a transport passage 331 of the post-analysis rack holding section 330 by a rack pushing mechanism 323. When optical sensors 332*a* and 332*b* including a light-emitting section and a light-receiving section detect the sample rack L on the transport passage 331, a rack sending mechanism 333 moves forward while coming into contact with the rear ends of the sample rack L and the sample rack L is sent to the front. At this time, a partition section 360 which is in front of the post-analysis rack holding section 330 and is between the rack transport sections 340 and 350 is controlled to be opened and closed and the sample rack L is positioned in either of the rack transport sections 340 or 350.

As a result of the measurement by the measuring unit 41, when it is determined that the smear preparation apparatus 6 on the downstream side needs to prepare smears related to any of sample containers T which are held in the sample rack L, the sample rack L moves up to the left end position of the rack transport section 340 by the rack sending mechanism 333 in a state in which the rack transport sections 340 and 350 are partitioned by the partition section 360. Then, the sample rack L is output to the sample transport unit on the downstream side by the belt 341*b* of the rack transport section 340.

On the other hand, as a result of the measurement by the measuring unit 41, when it is determined that the smear preparation apparatus 6 on the downstream side does not need to prepare smears related to any of the sample containers T which are held in the sample rack L, the upper side of the partition section 360 is dropped to be disposed at the same height as the upper side of the belt 341*b* of the rack transport section 340 and the sample rack L is moved up to the left end position of the rack transport section 350 by the rack sending mechanism 333. In this manner, by the rack sending mechanism 333, the sample rack L is moved across the rack transport section 340 from the post-analysis rack holding section 330 up to the left end position of the rack transport section 350, which is shown by the broken line in the left lower portion of FIG. 3. Then, the sample rack L is moved in the right direction along the transport line L3 by a belt 351 of the rack transport section 350. In this manner, the sample rack L which is transported along the transport line L3 is stored in the sample recovery unit 21.

When the operation mode of the measuring unit 41 corresponding to this sample transport unit 3 is the "single mode", an operator can directly set the sample rack L on the transport passage 311 so that the measurement is performed by the corresponding measuring unit 41. In this case also, when the sensors 312*a* and 312*b* detect the sample rack L, this sample rack L is transported along the transport line L1, and at the sample supply position, the measurement is performed on the samples in all the sample containers T held in the sample rack L. After that, the sample rack L is positioned at the rear end of the transport passage 331 of the post-analysis rack holding section 330. In this case, the sample rack L is not sent up to the transport section 340 or 350 by the rack sending mechanism 333, but is put on the transport passage 331.

In the sample transport unit 3, a stepping motor for driving the rack pushing mechanisms 343 and 323, the rack sending mechanisms 313 and 333, the belts 321*a*, 321*b*, 341*a*, 341*b* and 351 and the partition section 360 is disposed. In addition, in the sample transport unit 3, in addition to the sensors 342, 312*a*, 312*b*, 332*a* and 332*b* and the sample container sensor 322, a sensor for detecting the position of a sample rack L on the transport passage is disposed at a corresponding position.

The sample transport unit 5 also has almost the same configuration as that of the sample transport unit 3. In this case, when a sample rack L including a sample in which it is determined that the preparation of a smear is needed is transported to the sample transport unit 5, it is positioned at the sample supply position along the transport line L1 and the smear preparation apparatus 6 prepares a smear as in the measurement by the measuring unit 41. After that, it is transported in the right direction toward the sample recovery unit 21 along the transport line L3.

Figure 4:
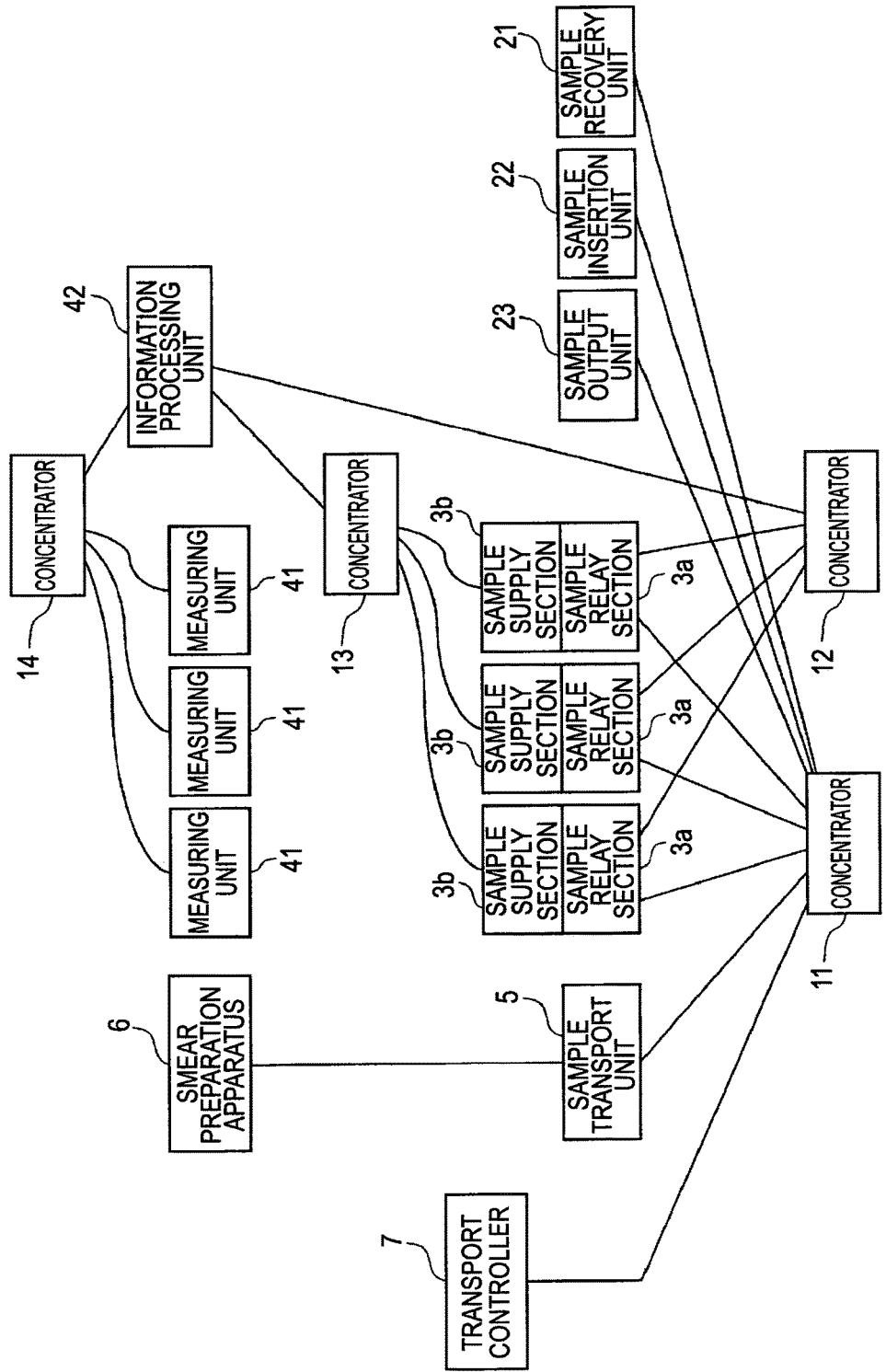
FIG. 4 is a diagram schematically showing the reciprocal connection relationship between the units (apparatuses) in the sample processing system according to the embodiment.

FIG. 4 is a diagram schematically showing the reciprocal connection relationship between the units (apparatuses) in the sample processing system 1.

Here, in the drawing, the three sample transport units 3 are divided into a sample relay section 3*a* and a sample supply section 3*b*, respectively. In greater detail, the sample relay section 3*a* includes the post-analysis rack holding section 330 and the rack transport sections 340 and 350 of FIG. 3, and one of the neighboring two sample transport units 3 receives a sample rack L and transports it to the other sample transport unit 3. The sample supply section 3*b* includes the pre-analysis rack holding section 310 and the rack transport section 320 of FIG. 3 and transports a sample rack L to the sample supply position in order to measure a sample by the measuring unit 41.

The sample recovery unit 21, the sample insertion unit 22, the sample output unit 23, the three sample relay sections 3a, the sample transport unit 5 and the transport controller 7 are connected to a concentrator 11 so as to communicate therewith. The three sample relay sections 3a and the information processing unit 42 are connected to a concentrator 12 so as to communicate therewith.

The three sample supply sections 3b and the information processing unit 42 are connected to a concentrator 13 so as to communicate therewith. The three measuring units 41 and the information processing unit 42 are connected to a concentrator 14 so as to communicate therewith.

Figure 5:
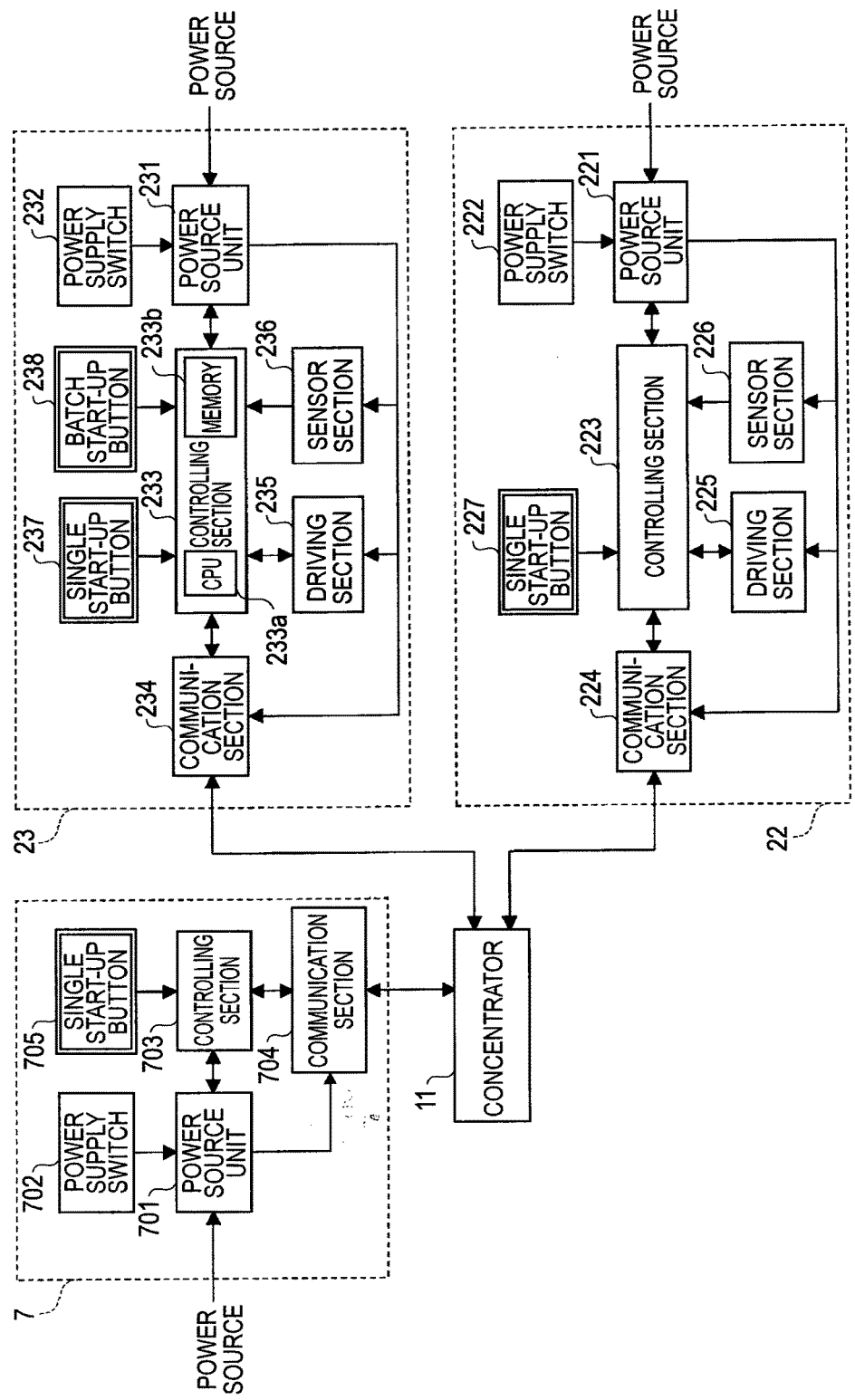
FIG. 5 is a diagram showing the outline of the circuit configurations of a sample insertion unit, a sample output unit and a transport controller according to the embodiment.

FIG. 5 is a diagram showing the outline of the circuit configurations of the sample insertion unit 22, the sample output unit 23 and the transport controller 7.

The sample output unit 23 includes a power source unit 231, a power supply switch 232, a controlling section 233, a communication section 234, a driving section 235, a sensor section 236, a single start-up button 237 and a batch start-up button 238.

The power source unit 231 is supplied with power from the outside. When the power supply switch 232 is in the ON condition, the power source unit 231 can supply power to the sections in the sample output unit 23 as shown in FIG. 5. In the following description, the power supply switch 222 is always in the ON condition.

The controlling section 233 executes a computer program stored in a memory 233b by a CPU 233a in the controlling section 233 and controls the sections singly or in accordance with a controlling section of the transport controller 7. Another controlling section to be described later also includes a CPU and a memory. The communication section 234 includes a communication interface for performing data communication with an external apparatus on the basis of Ethernet (registered trademark) standards and performs data communication with the concentrator 11.

The driving section 235 is controlled by the controlling section 233. In the driving section 235, a mechanism for transporting a sample rack L which is stored in the sample output unit 23 and a stepping motor for driving this mechanism are included. The sensor section 236 outputs a detection signal to the controlling section 233. In the sensor section 236, a bar-code reading section 23a is included in addition to a sensor for detecting a sample rack L which is stored in the sample output unit 23 is included.

The single start-up button 237 is a button for singly starting up the sample output unit 23. When the single start-up button 237 is pressed, the start-up process is performed and thus the sample output unit 23 is started up.

The batch start-up button 238 starts up all other units (apparatuses) directly or indirectly connected to the concentrator 11 in addition to the sample output unit 23. That is, when the batch start-up button 238 is pressed, first, the sample output unit 23 is started up as in the case in which the single start-up button 237 is pressed. After that, the controlling section 233 transmits data for start-up to the concentrator 11 via the communication section 234. When such data is received by the sample recovery unit 21, the sample insertion unit 22, the three sample relay sections 3a, the sample transport unit 5 and the transport controller 7 connected to the concentrator 11, the start-up process is performed in these units (apparatuses) and thus these units (apparatuses) are started up. In addition, the three sample supply sections 3b, the information processing unit 42, the three measuring units 41 and the smear preparation apparatus 6 are started up on the basis of data for start-up which is transmitted from the sample relay section 3a of the started-up sample transport unit 3 or a signal for start-up which is transmitted from the started-up sample transport unit 5.

As shown in FIG. 5, the sample insertion unit 22 has a circuit configuration in which the batch start-up button 238 is removed from the sample output unit 23.

A power source unit 221 is supplied with power from the outside. A power supply switch 222 is always in the ON condition and the power source unit 221 can supply power to the sections in the sample insertion unit 22.

Here, the state in which the sample insertion unit 22 is not started up is a state in which power is supplied only to a controlling section 223 and a communication section 224 from the power source unit 221. In this state, when the batch start-up button 238 of the sample output unit 23 is pressed, the sample insertion unit 22 is started up. That is, when the batch start-up button of the sample output unit 23 is pressed and data for start-up is transmitted to the concentrator 11, the controlling section 223 of the sample insertion unit 22 receives the data for start-up via the communication section 224. When receiving the data for start-up, the controlling section 223 starts up the sample insertion unit 22 as in the case in which a single start-up button 227 is pressed.

In addition, when the sample insertion unit 22 is being started up, in the case in which data for start-up is received or the single start-up button 227 is pressed, the sample insertion unit 22 maintains its state without change.

As shown in the drawing, the transport controller 7 has a circuit configuration in which a driving section 225 and a sensor section 226 are removed from the sample insertion unit 22. In this case also, as in the sample insertion unit 22, when the batch start-up button 238 of the sample output unit 23 is pressed, data for start-up is transmitted to the transport controller 7 via the concentrator 11 and the transport controller 7 is started up from a non-start-up state.

The sample recovery unit 21 also has the same circuit configuration as that of the sample insertion unit 22, and when the batch start-up button 238 of the sample output unit 23 is pressed, data for start-up is transmitted to the sample recovery unit 21 via the concentrator 11. When receiving the data for start-up in a state in which the sample recovery unit 21 is not started up, a controlling section of the sample recovery unit 21 starts up the sample recovery unit 21 as in the case in which the single start-up button is pressed. In this manner, the sample recovery unit 21 is started up from a non-start-up state.

Figure 6:
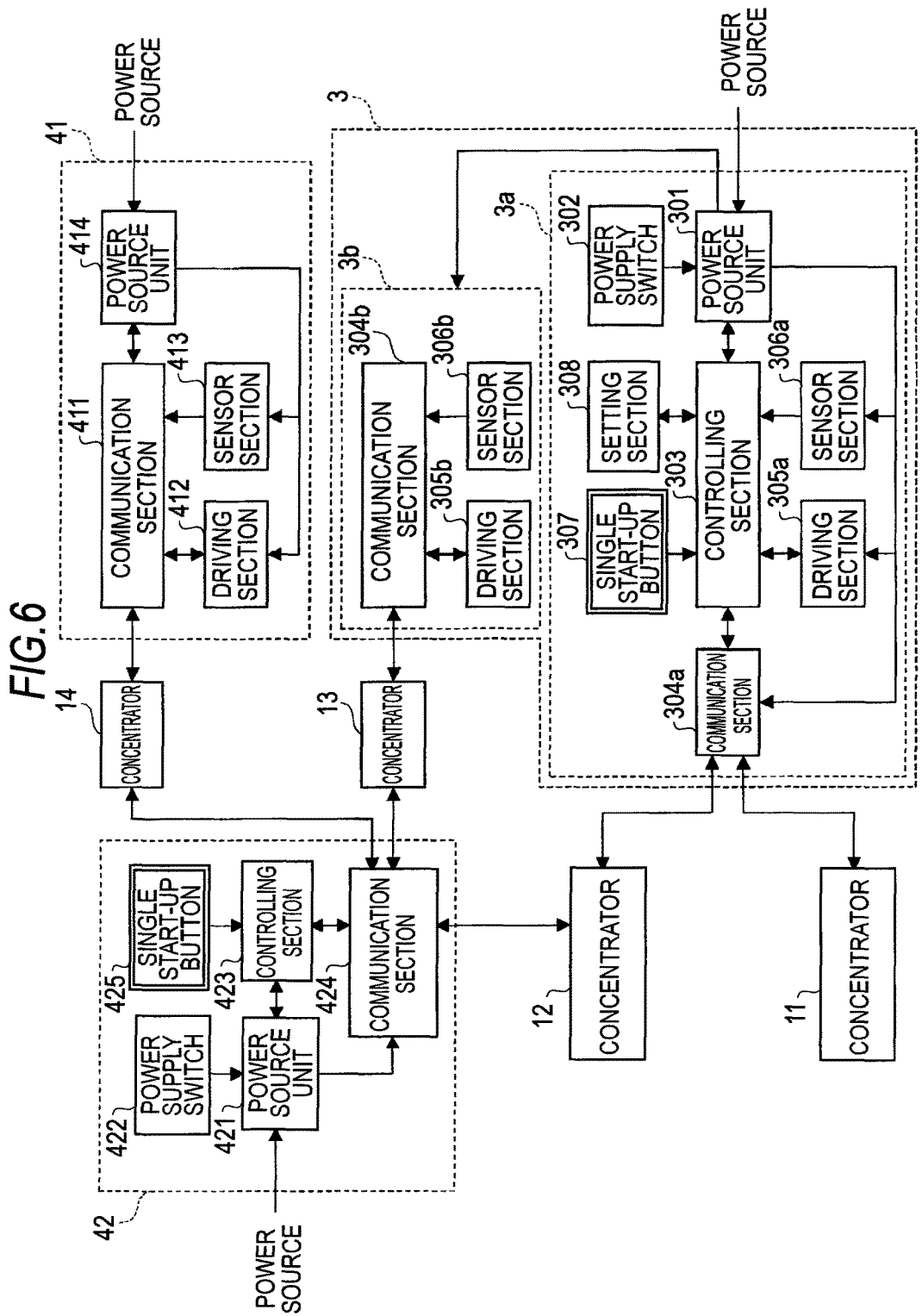
FIG. 6 is a diagram showing the outline of the circuit configurations of the sample transport unit, a measuring unit and an information processing unit according to the embodiment.

FIG. 6 is a diagram showing the outline of the circuit configurations of the sample transport unit 3, the measuring unit 41 and the information processing unit 42. In FIG. 6, for the sake of convenience, only one sample transport unit 3 and only one measuring unit 41 are shown. However, the other sample transport units 3 and the other measuring units 41 also have the same configurations.

The sample transport unit 3 has a circuit configuration in which a communication section 304b, a driving section 305b, a sensor section 306b and a setting section 308 are added from the sample transport unit 22 of FIG. 5.

A communication section 304a performs data communication between the concentrators 11 and 12 and the communication section 304b performs data communication with the concentrator 13. A driving section 305a is controlled by a controlling section 303 and the driving section 305b is controlled by the information processing unit 42 via the communication section 304b. A sensor section 306a outputs a detection signal to the controlling section 303 and the sensor section 306b outputs a detection signal to the information processing unit 42 via the communication section 304b.

The communication section 304b, the driving section 305b and the sensor section 306b are included in the sample supply section 3b of FIG. 4, and the sections in the sample transport unit 3 shown in FIG. 6, other than the communication section 304b, the driving section 305b and the sensor section 306b, are included in the sample relay section 3a of FIG. 4. The driving section 305a and the sensor section 306a include a mechanism for transporting and a mechanism for detecting sample racks L on the post-analysis rack holding section 330 and the rack transport sections 340 and 350 of FIG. 3, respectively. The driving section 305b and the sensor section 306b include a mechanism for transporting and a mechanism for detecting sample racks L on the pre-analysis rack holding section 310 and the rack transport section 320 of FIG. 3, respectively.

A power source unit 301 can supply power to the sections in the sample transport unit 3. In addition, when the sample transport unit 3 is not started up, power is not supplied to the sample supply section 3b from the power source unit 301.

Here, when the batch start-up button 238 of the sample output unit 23 is pressed, the controlling section 303 receives data for start-up from the concentrator 11 as in the sample insertion unit 22 and the sample relay section 3a of the sample transport unit 3 is started up. In addition, when the controlling section 303 receives the data for start-up, power is supplied to the sample supply section 3b from the power source unit 301 and thus the sample supply section 3b can receive an instruction from the information processing unit 42. When the sample transport unit 3 is started up, the controlling section 303 transmits data for start-up to the information processing unit 42 via the concentrator 12.

On the other hand, when the single start-up button 307 is pressed and the sample transport unit 3 is thus started up, the operation mode of the measuring unit 41 corresponding to this sample transport unit 3 is set to the "single mode". In addition, when the sample transport unit 3 is started up, the sample relay section 3a is started up and the sample supply section 3b can receive an instruction from the information processing unit 42. In this case also, the controlling section 303 of the sample transport unit 3 transmits data for start-up to the information processing unit 42 via the concentrator 12.

The setting section 308 includes a LED or a button. An operator can set the operations of the sample transport unit 3 and the measuring unit 41 corresponding to this sample transport unit 3 by manipulating a button which is disposed in the setting section 308. The setting section 308 will be described later with reference to FIG. 8.

The measuring unit 41 includes a communication section 411, a driving section 412, a sensor section 413 and a power source unit 414. The communication section 411 performs data communication with the concentrator 14. The driving section 412 and the sensor section 413 include a mechanism for transporting and a mechanism for detecting sample containers T in the measuring unit 41, respectively. The power source unit 414 is supplied with power from the outside. The power source unit 414 supplies power only to the communication section 411 when the measuring unit 41 is not started up. In addition, when receiving a signal for start-up from a controlling section 423 of the information processing unit 42 via the communication section 411, the concentrator 14 and a communication section 424, the power source unit 414 supplies power to the driving section 412 and the sensor section 413 and thus starts up the measuring unit 41.

The information processing unit 42 has the same circuit configuration as that of the transport controller 7 of FIG. 5. The controlling section 423 of the information processing unit 42 starts up the information processing unit 42 from a non-start-up state when receiving data for start-up from the controlling section 303 of the sample transport unit 3 via the concentrator 12.

When the information processing unit 42 is started up, the controlling section 423 controls the sample supply section 3b of the sample transport unit 3 via the communication section 424 and the concentrator 13 and receives a detection signal of the sensor section 306b. In addition, the controlling section 423 controls the driving section 412 of the measuring unit 41 via the communication section 424 and the concentrator 14 and receives a detection signal of the sensor section 413.

Figure 7:
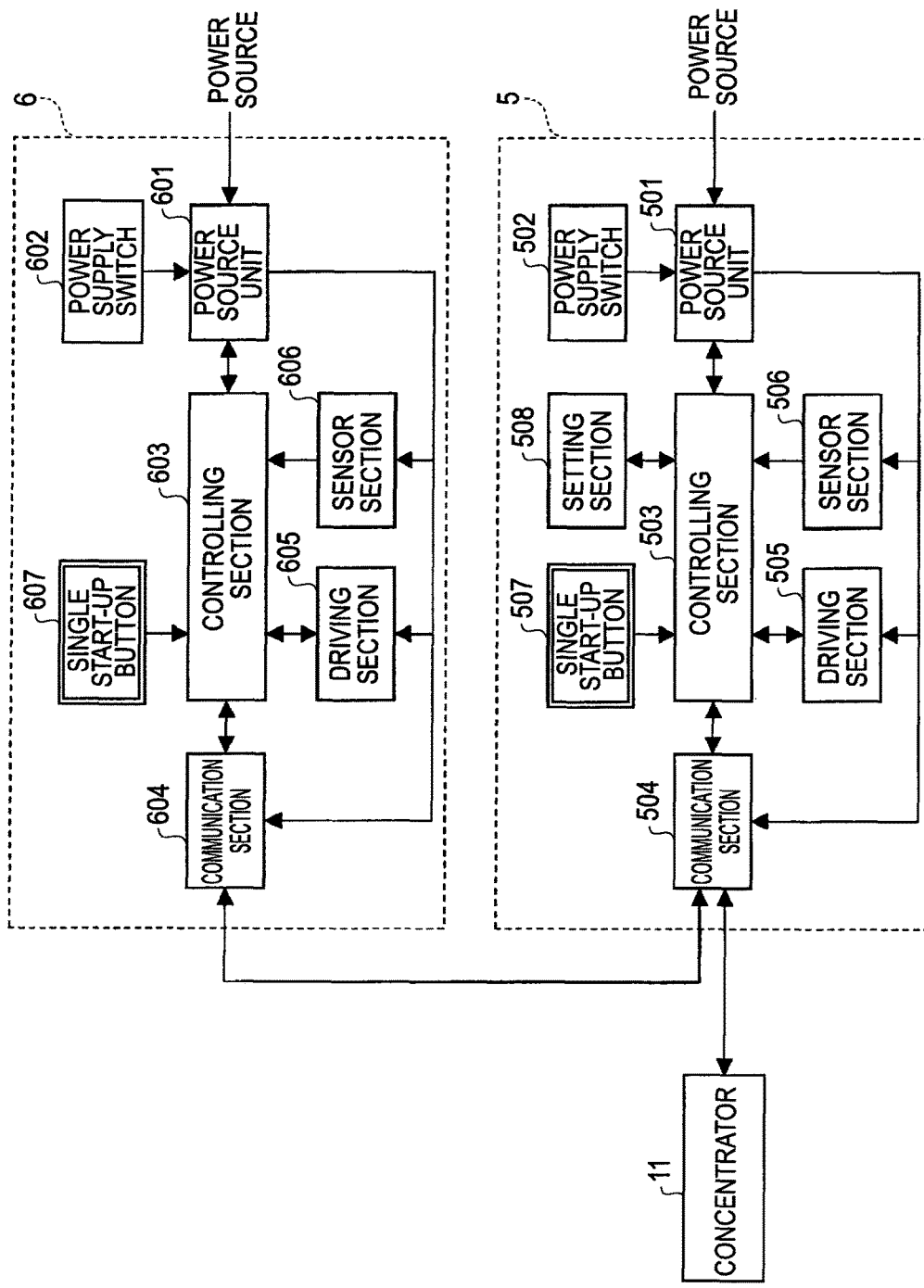
FIG. 7 is a diagram showing the outline of the circuit configurations of the sample transport unit and a smear preparation apparatus according to the embodiment.

FIG. 7 is a diagram showing the outline of the circuit configurations of the sample transport unit 5 and the smear preparation apparatus 6. The sample transport unit 5 has a circuit configuration in which a setting section 508 is added to the sample insertion unit 22 of FIG. 5 and the smear preparation apparatus 6 has the same circuit configuration as that of the sample insertion unit 22 of FIG. 5.

A communication section 504 of the sample transport unit 5 performs data communication with the concentrator 11. Accordingly, when the batch start-up button 238 of the sample output unit 23 is pressed, a controlling section 503 receives data for start-up via the concentrator 11 and starts up the sample transport unit 5.

In addition, the communication section 504 is connected to a communication section 604 of the smear preparation apparatus 6 via a signal line and performs data communication with the communication section 604. When the sample transport unit 5 is started up, a signal for start-up is transmitted to the communication section 604 from the communication section 504. A controlling section 603 of the smear preparation apparatus 6 starts up the smear preparation apparatus 6 when receiving a signal for start-up from the sample transport unit 5 via the communication section 604.

The setting section 508 has the same configuration as that of the setting section 308 of the sample transport unit 3 of FIG. 6. An operator can set the operations of the sample transport unit 5 and the smear preparation apparatus 6 by manipulating a button which is disposed in the setting section 508.

Figure 8:
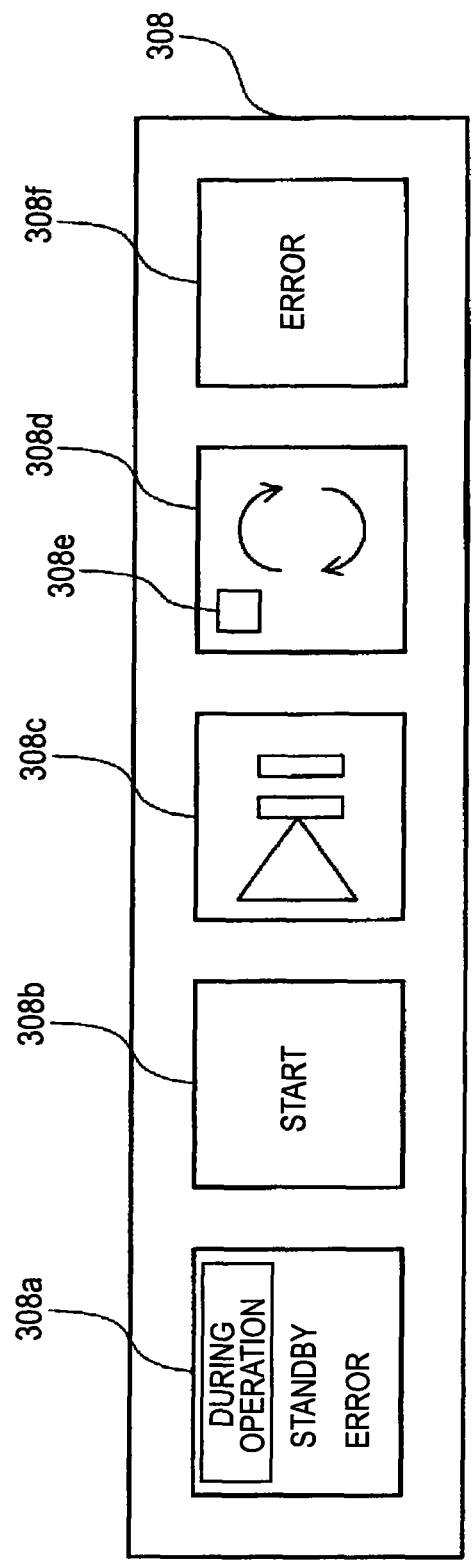
FIG. 8 is a diagram showing a setting section of the sample transport unit according to the embodiment.

FIG. 8 is a diagram showing the setting section 308 of the sample transport unit 3.

The setting section 308 includes an operation state display area 308a, a start button 308b, a stop button 308c, a mode switching button 308d and an error reset button 308f. In addition, the setting section 308 is installed on the front side of the sample transport unit 3.

The operation state display area 308a shows the operation state of the measuring unit 41 corresponding to this sample transport unit 3. On the operation state display area 308a, any of the words "during operation", "standby" and "error" is boxed and displayed as the operation state. In addition, when this sample transport unit 3 is not started up, none of the words is boxed and displayed. The example of FIG. 8 shows that the operation state of the measuring unit 41 corresponding to the sample transport unit 3 which is provided with this setting section 308 is the during operation. The operation state is stored in the memory in the controlling section of each sample transport unit 3 and is updated as needed.

Here, the "during operation" is a state in which the sample transport unit 3 and the measuring unit 41 corresponding thereto normally operate and the sample rack L is positioned in the area of any of the pre-analysis rack holding section 310, the rack transport section 320 and the post-analysis rack holding section 330 of the sample transport unit 3. The "standby" is a state in which the sample transport unit 3 and the measuring unit 41 corresponding thereto normally operate and the sample rack L is not positioned in the area of any of the pre-analysis rack holding section 310, the rack transport section 320 and the post-analysis rack holding section 330 of the sample transport unit 3. The "error" is a state in which the sample transport unit 3 or the measuring unit 41 corresponding thereto does not normally operate.

The controlling section 303 of the sample transport unit 3 obtains whether the sensor section 306*b* (see FIG. 6) has detected the sample rack L in order to obtain whether the sample rack L is positioned in the pre-analysis rack holding section 310 and the rack transport section 320 of the sample transport unit 3. In this case, the controlling section 303 inquires of the controlling section 423 of the information processing unit 42 which receives a detection signal output from the sensor section 306*b* and thus obtains whether the sensor section 306*b* has detected the sample rack L.

When the operation mode of the measuring unit 41 corresponding to this sample transport unit 3 is the "single mode", the sample rack L, which is set on the transport passage 311 of the pre-analysis rack holding section 310, is transported along the transport line L1 when the start button 308*b* is pressed, and the measurement is started by the corresponding measuring unit 41.

When the stop button 308*c* is pressed, the transportation of the sample racks L in the areas of the pre-analysis rack holding section 310, the rack transport section 320 and the post-analysis rack holding section 330 of this sample transport unit 3 is stopped. In addition, when the stop button 308*c* is pressed once again during the stop, the stop is released.

When the mode switching button 308*d* is pressed, the operation mode of the measuring unit 41 corresponding to this sample transport unit 3 is switched between the "single mode" and the "system mode". In addition, a LED 308*e* is disposed in the mode switching button 308*d*. The LED 308*e* is lighted in a red color when the current operation mode is the "single mode", and is turned off when the current operation mode is the "system mode". In addition, the operation mode of the measuring unit 41 is stored in the memory in the controlling section 303 of the corresponding sample transport unit 3.

When the error reset button 308*f* is pressed, the alarm is released when this sample transport unit 3 or the measuring unit 41 corresponding thereto is in the "error" state.

Hereinafter, the process (hereinafter, simply referred to as the "start-up process") when the batch start-up button 238 of the sample output unit 23 is pressed will be described. In this embodiment, even when the batch start-up button 238 is pressed plural times, the second and subsequent pressing manipulation is valid and the start-up process is executed. In addition, when the single start-up button of each apparatus or unit is pressed, the apparatus or unit is singly started up as described above. When the sample transport unit 3 is singly started up, the measuring unit 41 corresponding to this sample transport unit 3 is set to the single mode. In addition, although the single start-up button is pressed when each apparatus or unit is in a start-up state, the pressing manipulation is invalid.

FIG. 9A is a flowchart showing the start-up process of the sample output unit 23.

When the batch start-up button 238 of the sample output unit 23 is pressed (S11: YES), the controlling section 233 determines whether the sample output unit 23 is already in a start-up state (S12). When the sample output unit 23 is not in a start-up state (S12: YES), the controlling section 233 starts up the sample output unit 23 (S13). On the other hand, when the sample output unit 23 is in a start-up state (S12: NO), the controlling section 233 maintains a start-up state. After that, the controlling section 233 transmits data for start-up (start-up command signal) to the sample recovery unit 21, the sample insertion unit 22, the three sample transport units 3, the sample transport unit 5 and the transport controller 7 (S14) and completes the process.

FIG. 9B is a flowchart showing the start-up process of the sample insertion unit 22.

When the sample insertion unit 22 receives data for start-up (start-up command signal) which is transmitted from the sample output unit 23 (S21: YES), the controlling section 223 of the sample insertion unit 22 determines whether the sample insertion unit 22 is already in a start-up state (S22). When the sample insertion unit 22 is not in a start-up state (S22: YES), the controlling section 233 starts up the sample insertion unit 22 (S23). On the other hand, when the sample insertion unit 22 is in a start-up state (S22: NO), the controlling section 223 maintains a start-up state. In this manner, the process is completed.

FIG. 9C is a flowchart showing the start-up process of the sample recovery unit 21.

When the sample recovery unit 21 receives data for start-up (start-up command signal) which is transmitted from the sample output unit 23 (S31: YES), the controlling section of the sample recovery unit 21 determines whether the sample recovery unit 21 is already in a start-up state (S32). When the sample recovery unit 21 is not in a start-up state (S32: YES), the controlling section of the sample recovery unit 21 starts up the sample recovery unit 21 (S33). On the other hand, when the sample recovery unit 21 is in a start-up state (S32: NO), the controlling section of the sample recovery unit 21 maintains a start-up state. In this manner, the process is completed.

FIG. 10A is a flowchart showing the start-up process of the sample transport unit 3.

When this sample transport unit 3 receives data for start-up (start-up command signal) which is transmitted from the sample output unit 23 (S41: YES), the controlling section 303 of the sample output unit 3 determines whether this sample transport unit 3 is already in a start-up state (S42). When the sample transport unit 3 is not in a start-up state (S42: YES), the controlling section 303 starts up this sample transport unit 3 (S43) and sets the operation mode of the corresponding measuring unit 41 to the "system mode" (S44). After that, by the controlling section 303, data for start-up (start-up command signal) is transmitted to the information processing unit 42 (S45). On the other hand, when it is determined that the sample transport unit 3 is being started up (S42: NO), a "mode setting and notification" process is performed (S46).

In addition, in S45, the data for start-up (start-up command signal) may be transmitted to the information processing unit 42 by the three sample transport units 3 and may be transmitted to the information processing unit 42 only by any of the sample transport units 3.

As described above, when the sample transport unit 3 is started up by pressing the single start-up button 307 of the sample transport unit 3, the operation mode of the corresponding measuring unit 41 is set to the "single mode".

FIG. 10B is a process flowchart showing the "mode setting and notification".

When the operation mode of the measuring unit 41 corresponding to the sample transport unit 3 is the "single mode" (S101: YES), the controlling section 303 of this sample transport unit 3 obtains the operation state of the corresponding measuring unit 41 (S102). That is, in S102, whether the operation state of the corresponding measuring unit 41 is the "during operation", the "standby" or the "error" is obtained. On the other hand, when the operation mode of the measuring unit 41 corresponding to the sample transport unit 3 is the "system mode" (S101: NO), the process proceeds to S107.

Next, when the operation state of the measuring unit 41 corresponding to this sample transport unit 3 is not the "standby" (S103: NO), the single mode is maintained (S104). In this case, the state of the LED 308*e* of the setting section 308 is maintained to be a red-color light state showing that the operation mode of the measuring unit is the "single mode". In addition, the controlling section 303 transmits data showing that the operation mode of the corresponding measuring unit 41 is the "single mode" to the transport controller 7 (S105).

On the other hand, when the operation state of the measuring unit 41 corresponding to this sample transport unit 3 is the "standby" (S103: YES), the controlling section 303 changes the operation mode of the corresponding measuring unit 41 to the "system mode" (S106) and the LED 308*e* of the setting section 308 is turned off to show that the operation mode of the corresponding measuring unit 41 is the "system mode" (S107). Next, the controlling section 303 transmits data showing that the operation mode of the corresponding measuring unit 41 is the "system mode" to the transport controller 7 (S108). In this manner, the "mode setting and notification" process is completed.

The flowcharts shown in FIGS. 10A and 10B are also applied to the start-up process of the sample transport unit 5. In this case, in S45 of FIG. 10A, the control device 503 of the sample transport unit 5 transmits a signal for start-up to the smear preparation apparatus 6. Accordingly, the smear preparation apparatus 6 becomes in a start-up state. In addition, in S102 of FIG. 10B, the operation state of the smear preparation apparatus 6 is obtained, and in S103, it is determined whether the smear preparation apparatus 6 is on standby.

FIG. 11A is a flowchart showing the start-up process of the transport controller 7.

When the transport controller 7 receives data for start-up (start-up command signal) which is transmitted from the sample output unit 23 (S51: YES), a controlling section 703 of the transport controller 7 determines whether the transport controller 7 is already in a start-up state (S52). When the transport controller 7 is not in a start-up state (S52: YES), the controlling section 703 starts up the transport controller 7 (S53). On the other hand, when the transport controller 7 is in a start-up state (S52: NO), the controlling section 703 maintains a start-up state.

Next, when the transport controller 7 receives information on the operation mode transmitted in S105 or S108 of FIG. 10B from the three sample transport units 3 (S54: YES), the controlling section 703 stores the operation mode of the corresponding measuring unit 41 in the memory in the controlling section 703 on the basis of the information on the received operation mode (S55). In this manner, the process is completed. In addition, when the operation modes of all the measuring units 41 are not received within a predetermined time, the controlling section 703 stores only the received operation modes of the measuring units 41 in the memory in the controlling section 703.

FIG. 11B is a flowchart showing the start-up process of the information processing unit 42.

When the information processing unit 42 receives data for start-up (start-up command signal) which is transmitted from the sample transport unit 3 (S61: YES), the controlling section 423 of the information processing unit 42 determines whether the information processing unit 42 is already in a start-up state (S62). When the information processing unit 42 is not in a start-up state (S62: YES), the controlling section 423 starts up the information processing unit 42 (S63). On the other hand, when the information processing unit 42 is in a start-up state (S62: NO), the controlling section 423 maintains a start-up state.

After that, the controlling section 423 transmits a signal (start-up command signal) for starting up the measuring unit 41 to each measuring unit 41 (S64). At this time, the start-up state is maintained in the measuring unit 41 which is already in a start-up state. Accordingly, all the measuring units 41 are in a start-up state. In this manner, the process is completed.

FIG. 11C is a flowchart showing the start-up process of the smear preparation apparatus 6.

When the smear preparation apparatus 6 receives a signal for start-up (start-up command signal) which is transmitted from the sample transport unit 5 (S71: YES), the controlling section 603 of the smear preparation apparatus 6 determines whether the smear preparation apparatus 6 is already in a start-up state (S72). When the smear preparation apparatus 6 is not in a start-up state (S72: YES), the controlling section 603 starts up the smear preparation apparatus 6 (S73). On the other hand, when the smear preparation apparatus 6 is in a start-up state (S72: NO), the controlling section 603 maintains a start-up state. In this manner, the process is completed.

Next, the transport control of a sample rack L by the transport controller 7 will be described.

FIG. 12A is a flowchart for determination of the destination of a sample rack L which is output from the sample output unit 23.

The controlling section 703 of the transport controller 7 reads the operation modes of the measuring units 41 which are stored in the controlling section 703 and selects the measuring units 41 of which the operation mode is the "system mode" (S201). Next, the controlling section 703 confirms the acceptance circumstances for the sample rack L of the measuring units 41 selected in S201 (S202). Such confirmation of the acceptance circumstances is performed on the basis of detection signals of the sensors 312*a* and 312*b* of the pre-analysis rack holding section 310 of the sample transport unit 3 corresponding to this measuring unit 41. That is, when there is a sample rack L on the transport passage 311 of the pre-analysis rack holding section 310, it is determined that this measuring unit 41 cannot accept the sample rack L. When there is no sample rack L on the transport passage 311 of the pre-analysis rack holding section 310, it is determined that this measuring unit 41 can accept the sample rack L.

Through the confirmation of these acceptance circumstances of S202, when determining that any of the measuring units 41 selected in S201 can accept the sample rack L (S203: YES), the controlling section 703 determines the measuring unit 41 capable of accepting the sample rack as the destination of the sample rack L among the selected measuring units (S204) and completes the process. On the other hand, when determining that all the measuring units 41 selected in S201 cannot accept the sample rack L (S203: NO), the controlling section 703 returns the process to S201 and waits that any of the measuring units 41 selected in S201 can accept the sample rack L. When it is determined that the plural measuring units 41 can accept the sample rack in S202, the measuring unit 41 on the downstream side (left side) is decided as the transport destination.

FIG. 12B is a flowchart showing the process in the sample transport unit 3 when the operation mode switching manipulation is carried out. This process flowchart is also applied to the sample transport unit 5.

When the mode switching button 308d disposed in the setting section 308 of the sample transport unit 3 is pressed (S301: YES), the controlling section 303 of the sample transport unit 3 switches the display on the LED 308e (S302), and further, switches the operation mode (S303). That is, if the mode switching button 308d is pressed when the operation mode is the "system mode", the LED 308e is lighted and the operation mode is switched to the "single mode". In addition, if the mode switching button 308d is pressed when the operation mode is the "single mode", the LED 308e is turned off and the operation mode is switched to the "system mode". Further, the controlling section 303 transmits data for notifying the operation mode after the switching (mode change notice) to the transport controller 7 (S304). In this manner, the process in the transport unit 3 is completed.

FIG. 12C is a flowchart showing the process in the transport controller 7 when the operation mode switching manipulation is carried out.

When receiving a mode change notice (refer to S304 of FIG. 12B) from the sample transport unit 3 (S401), the transport controller 7 updates the operation mode of the measuring unit 41 corresponding to the sample transport unit 3 which is the transmission source of the notice to the operation mode corresponding to the received mode change notice (S402).

In this manner, when the operation mode is changed, the process in S201 of FIG. 12A is performed on the basis of the operation mode after the change. Accordingly, when the operation mode of a predetermined measuring unit 41 is switched to the "single mode", the measuring units 41 excluding this measuring unit 41 are subjected to the transport control of S202 to S204. In addition, when the operation mode of a predetermined measuring unit 41 is switched to the "system mode", the measuring units 41 including this measuring unit 41 are subjected to the transport control of S202 to S204. In this manner, by appropriately manipulating the mode switching button 308d, an operator can set the corresponding measuring unit 41 to be used through the automatic transport or separately.

According to this embodiment, an operator can start up the units (apparatuses) in a batch by pressing the batch start-up button 238 of the sample output unit 23. Accordingly, the operator does not need to perform the start-up manipulation separately on the units (apparatuses) in the sample processing system 1 and the start-up manipulation of the operator can be simplified.

In addition, according to this embodiment, a sample rack L which is output from the sample output unit 23 is not positioned in the smear preparation apparatus 6 and the measuring unit 41 in which the operation mode is the "single mode". Accordingly, the smear preparation apparatus 6 and the measuring unit 41 in which the operation mode is the "single mode" are maintained in a state so as to be capable of being used separately. Therefore, an urgent smear preparation or sample measurement can be performed in the smear preparation apparatus 6 and the measuring unit 41 in which the operation mode is the "single mode".

In addition, according to this embodiment, when the mode switching button of the setting section is pressed, the operation modes of the measuring unit 41 and the smear preparation apparatus 6 are switched between the "single mode" and the "system mode". Accordingly, an operator can easily change the operation modes of the smear preparation apparatus 6 and the measuring unit 41 in which the operation mode is set to any of the modes without re-start or the like.

Although the embodiments of the present invention have been described, the embodiments of the present invention are not limited thereto.

For example, in the above-described embodiments, blood is exemplified as a measurement target. However, urine can also be a measurement target. That is, the present invention can also be applied to a sample processing apparatus examining urine, and further, the present invention can also be applied to clinical sample examination apparatuses examining other clinical samples.

In addition, in the above-described embodiments, the units (apparatuses) are started up by pressing the batch start-up button 238 of the sample output unit 23. However, the present invention is not limited thereto and the button for batch start-up may be disposed in a unit (apparatus) other than the sample output unit 23. In addition, the units (apparatuses) may be started up by any of the units (apparatuses) receiving data for start-up (start-up command signal) transmitted from outside the sample processing system 1.

In addition, in the above-described embodiments, when the batch start-up button 238 of the sample output unit 23 is pressed, data for start-up (start-up command signal) is transmitted to the sample recovery unit 21, the sample insertion unit 22, the three sample transport units 3, the sample transport unit 5 and the transport controller 7 from the sample output unit 23, and via these units (apparatuses), data for start-up (start-up command signal) is transmitted to the other units (apparatuses). However, the present invention is not limited thereto and data of start-up instruction may be directly transmitted to all the units (apparatuses) from the sample output unit 23.

In addition, in the above-described embodiments, when the batch start-up button 238 of the sample output unit 23 is pressed, data for start-up (start-up command signal) is transmitted to the sample recovery unit 21, the sample insertion unit 22, the three sample transport units 3, the sample transport unit 5 and the transport controller 7 from the sample output unit 23. However, the present invention is not limited thereto. Data for start-up (start-up command signal) may be transmitted to the transport controller 7 from the sample output unit 23 and data for start-up (start-up command signal) may be transmitted to the sample recovery unit 21, the sample insertion unit 22, the three sample transport units 3 and the sample transport unit 5 from the transport controller 7.

Figure 13B:
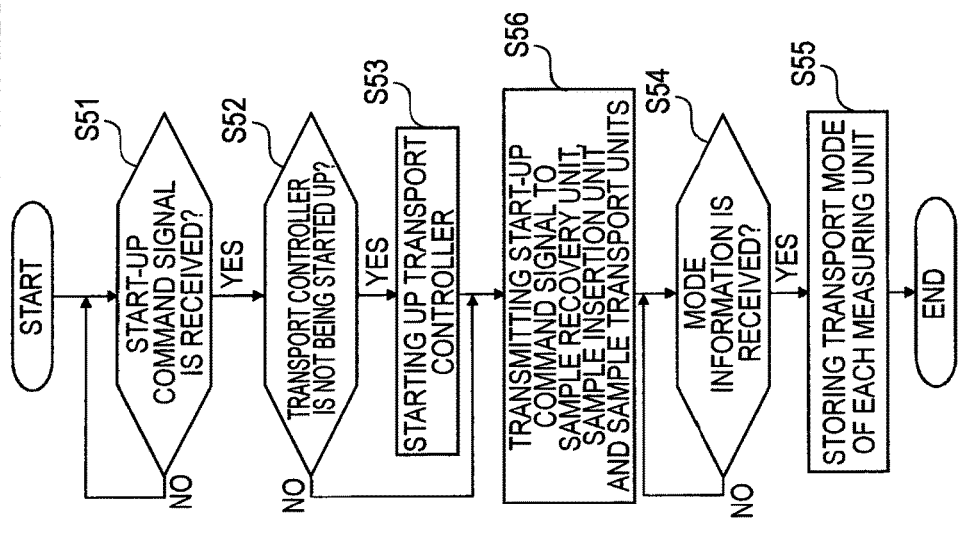
FIG. 13B is a modified example of the flowchart showing the start-up process of the transport controller according to the embodiment.
Figure 13A:
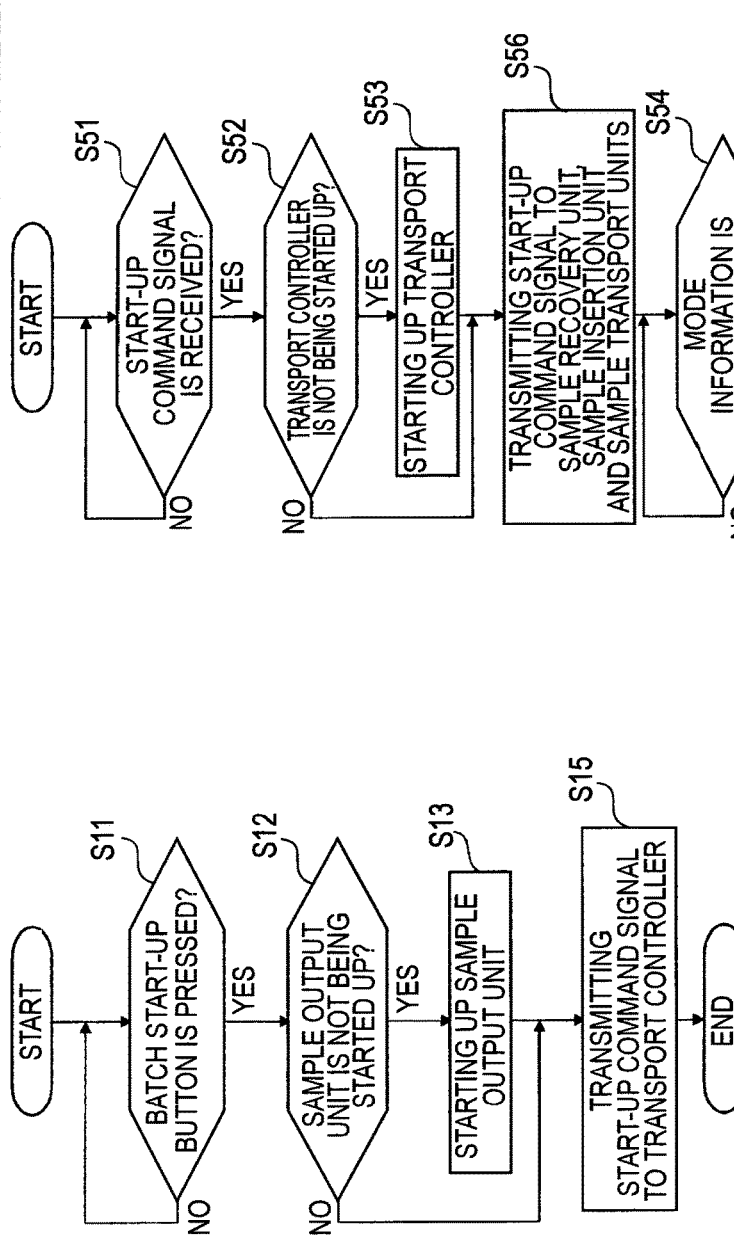
FIG. 13A is a modified example of the flowchart showing the start-up process of the sample output unit according to the embodiment.

FIG. 13A is a flowchart showing the start-up process of the sample output unit 23 in this case. In this flowchart, S14 in the flowchart shown in FIG. 9A is changed to S15. In S15, data for start-up (start-up command signal) is transmitted to the transport controller 7 from the sample output unit 23.

FIG. 13B is a flowchart showing the start-up process of the transport controller 7 in this case. In this flowchart, S56 is added under S53 in the flowchart shown in FIG. 11A. In S56, data for start-up (start-up command signal) is transmitted to the sample recovery unit 21, the sample insertion unit 22, the three sample transport units 3 and the sample transport unit 5 from the transport controller 7.

In addition, in the above-described embodiments, the units (apparatuses) are connected so as to communicate therewith as shown in FIG. 4. However, the present invention is not limited thereto. The sample output unit 23 and the information processing unit 42 are directly connected so as to communicate therewith and data for start-up (start-up command signal) may be transmitted to the information processing unit 42 from the sample output unit 23. In this case, data for start-up (start-up command signal) is transmitted to the sample transport unit 3 from the information processing unit 42 and data for start-up (start-up command signal) is transmitted to the sample recovery unit 21, the sample insertion unit 22, the sample transport unit 5 and the transport controller 7 from the sample transport unit 3.

Figure 14B:
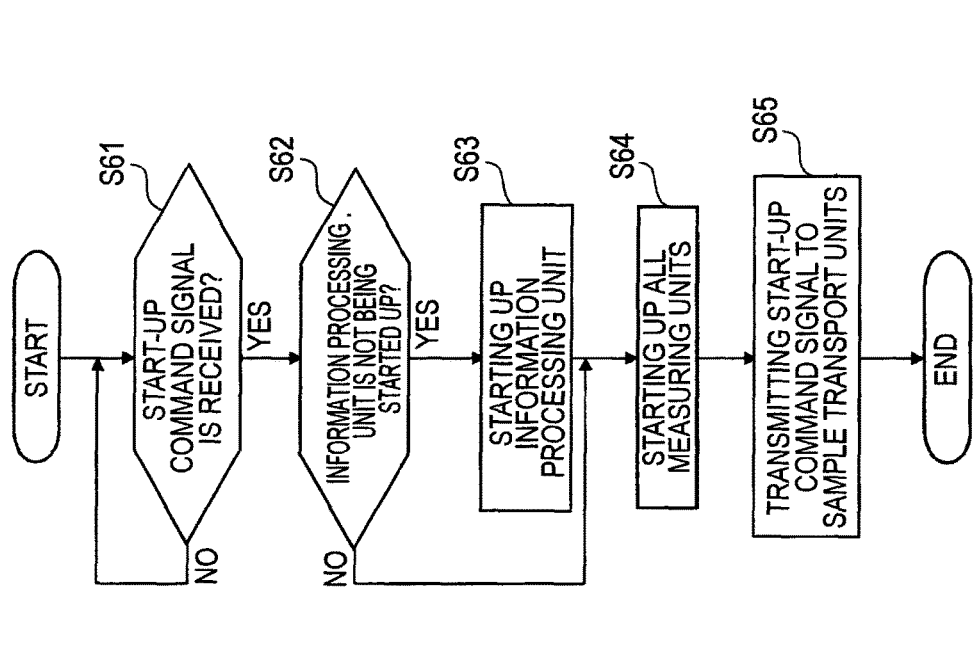
FIG. 14B is a modified example of the flowchart showing the start-up process of the information processing unit according to the embodiment.
Figure 14A:
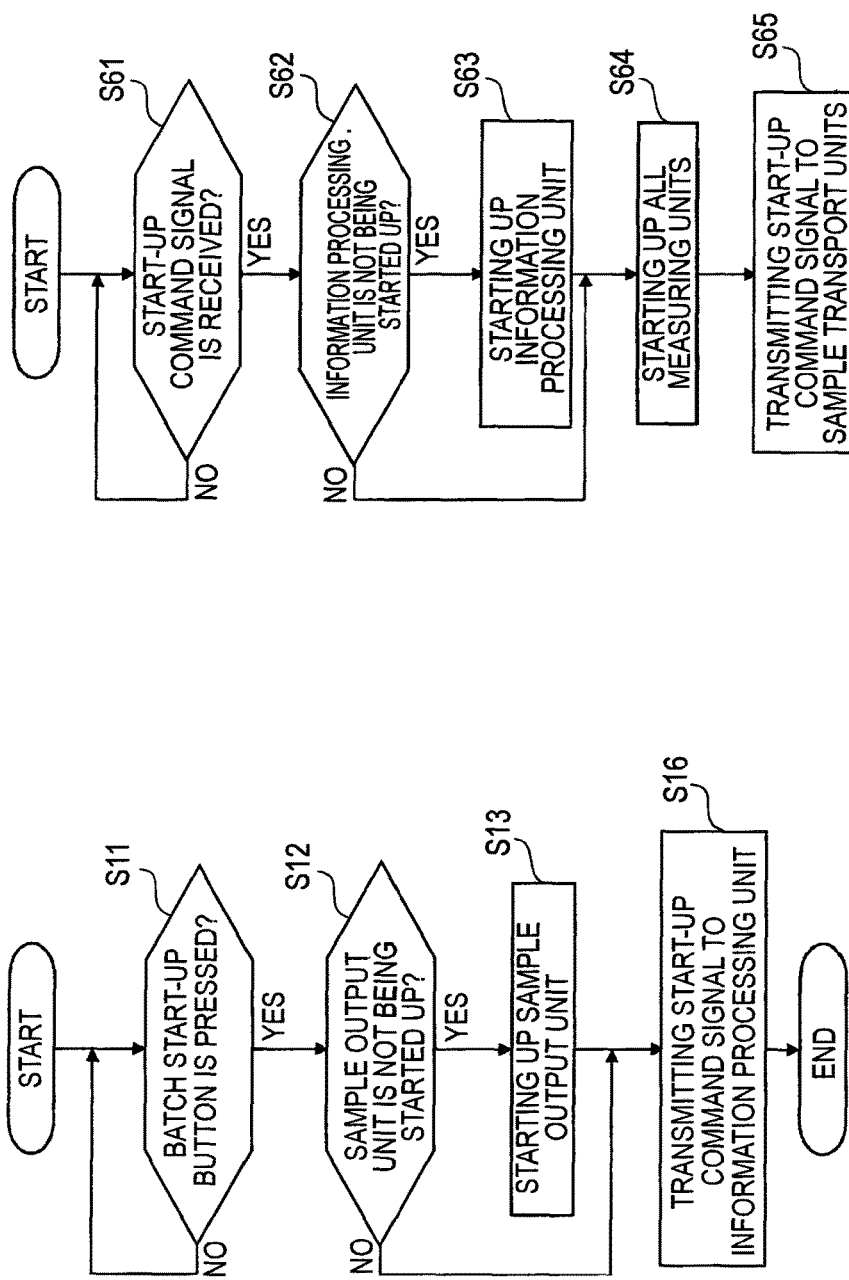
FIG. 14A is a modified example of the flowchart showing the start-up process of the sample output unit according to the embodiment.

FIG. 14A is a flowchart showing the start-up process of the sample output unit 23 in this case. In this flowchart, S14 in the flowchart shown in FIG. 9A is changed to S16. In S16, data for start-up (start-up command signal) is transmitted to the information processing unit 42 from the sample output unit 23.

FIG. 14B is a flowchart showing the start-up process of the information processing unit 42 in this case. In this flowchart, S65 is added under S64 in the flowchart shown in FIG. 11B. In S65, data for start-up (start-up command signal) is transmitted to the three sample transport units 3 from the information processing unit 42.

FIG. 15A is a flowchart showing the start-up process of the sample transport unit 3 in this case. In this flowchart, S47 is added under S45 in the flowchart shown in FIG. 10A. In S47, the controlling section 303 of the sample transport unit 3 transmits data for start-up (start-up command signal) to the sample recovery unit 21, the sample insertion unit 22, the sample transport unit 5 and the transport controller 7.

In addition, in S47, data for start-up (start-up command signal) may be transmitted by the three sample transport units 3, respectively, and may be transmitted only by any of the sample transport units 3.

In addition, in the above-described embodiments, data for start-up (start-up command signal) is transmitted to the three sample transport units 3 and the sample transport unit 5 from the sample output unit 23. However, the present invention is not limited thereto. Data for start-up (start-up command signal) may be transmitted to one or more sample transport units associated in advance among the three sample transport units 3 and the sample transport unit 5. In this case, the sample transport unit receiving the data for start-up (start-up command signal) transmits data for start-up (start-up command signal) to other sample transport units which do not receive the data for start-up (start-up command signal).

FIG. 15B is a flowchart showing the start-up process of the sample transport unit 3 receiving data for start-up (start-up command signal) in this case. In this flowchart, S48 is added under S45 in the flowchart shown in FIG. 10A. In S48, the controlling section 303 of this sample transport unit 3 transmits data for start-up (start-up command signal) to the other sample transport units 3 and the sample transport unit 5. In this case, the other sample transport units 3 and the sample transport unit 5 are subjected to the start-up process on the basis of the flowchart shown in FIG. 10A.

In addition, in the above-described embodiments, in S45 of FIG. 10A, each of the three sample transport units 3 transmits data for start-up (start-up command signal) to the information processing unit 42. However, the present invention is not limited thereto. Data for start-up (start-up command signal) may be transmitted to the information processing unit 42 from any one sample transport unit 3 of the three sample transport units 3.

In addition, in the above-described embodiments, when receiving the rack ID of a sample rack L, the sample ID of a sample container T and the holding position of the sample container T from the sample output unit 23, the transport controller 7 inquires of the host computer 8 for a measurement order. However, the present invention is not limited thereto, and when the measurement data corresponding to the sample ID is stored in a storage section 702b of the transport controller 7 and the transport controller 7 receives the data from the sample output unit 23, the transport controller 7 may read the measurement data corresponding to the received sample ID from the storage section 702b and transmit it to the sample output unit 23.

In addition, in the above-described embodiments, the sample recovery unit 21 is disposed on the right side of the sample insertion unit 22. However, the sample recovery unit may be disposed on the left side of the sample transport unit 5. In this case, a sample rack L in which analysis or the preparation of a smear has been ended is output to the left side of the sample transport unit 5 along the transport line L2 and is recovered in the sample recovery unit 21.

In addition, in the above-described embodiments, the controlling section 233 is provided in each sample transport unit 3. However, one controlling section 233 may control all the transport units 3 and 5. One controlling section 233 may further control the sample recovery unit 21, the sample insertion unit 22 and the sample output unit 23.

In addition, in the above-described embodiments, all the units (apparatuses) are started up by pressing the batch start-up button 238 of the sample output unit 23. However, the present invention is not limited thereto. Only some units may be started up and the remaining units may be started up by means of a user pressing the single start-up button.

The embodiments of the present invention can be appropriately and variously modified within the scope of the technical ideas shown in the claims.

What is claimed is:

1. A sample processing system comprising:
a plurality of sample processing units;
a plurality of transport units corresponding to the plurality of sample processing units and configured to transport a sample to the plurality of sample processing units, respectively;
a sample feeding unit configured to feed samples to the transport units;
a batch start-up button configured to trigger the transport units to activate in a system mode;
a mode switching button configured to switch one of the transport units activated in the system mode from the system mode to a single mode; and
at least one controller configured to control the transport units to distribute the samples fed from the sample feeding unit to the sample processing units corresponding to the transport units activated in the system mode via the transport units activated in the system mode, and to control the transport unit activated in the single mode to transport a sample manually set thereon to the sample processing unit corresponding to the transport unit activated in the single mode,
wherein the at least one controller is further configured to determine whether any transport unit activated in the single mode is in a standby state in response to a signal triggered via the batch start-up button, and to change the transport unit activated in the single mode to the system mode.

2. The sample processing system according to claim 1, wherein a first transport unit of the plurality of transport units comprises a start button that triggers the first transport unit to transport a sample and triggers a first sample processing unit of the plurality of sample processing units in the single mode to process the transported sample.

3. The sample processing system according to claim 1, wherein a first transport unit of the plurality of transport units comprises an indicator that indicates the operation mode of processing by lighting.

4. The sample processing system according to claim 3, wherein the first transport unit comprises a stop button that triggers the first transport unit to interrupt movement of the sample being transported.

5. The sample processing system according to claim 1, wherein a first transport unit of the plurality of transport units comprises an operation state display that displays an operation state of a first sample processing unit of the plurality of sample processing units.

6. The sample processing system according to claim 1, wherein the sample feeding unit is configured to feed the sample to a first transport unit of the plurality of transport units, the feeding unit comprising the batch start-up button.

7. The sample processing system according to claim 6, wherein the sample feeding unit includes an identification information reader configured to read an identification information of the sample.

8. The sample processing system according to claim 7, wherein the controller is in communication with a host computer and is configured to access the host computer to obtain a measurement order of the sample with the identification information.

9. The sample processing system according to claim 1, wherein a first sample processing unit of the plurality of transport units is configured to perform a first process on the sample, and
a second sample processing unit of the plurality of sample processing units is configured to perform a second sample process, which is different from the first process, on the sample.

10. The sample processing system according to claim 1, wherein a first transport unit of the plurality of transport units comprises a first communication section, and a first controlling section is in communication with the at least one controller via a first communication section; and
a second transport unit of the plurality of transport units comprises a second communication section, and a second controlling section is in communication with the at least one controller via a second communication section.

* * * * *